(12) United States Patent
Fu et al.

(10) Patent No.: US 8,921,657 B2
(45) Date of Patent: Dec. 30, 2014

(54) EXPRESSION CASSETTES FOR ENDOSPERM-SPECIFIC EXPRESSION IN PLANTS

(75) Inventors: Huihua Fu, Cary, NC (US); Jeffrey A. Brown, Apex, NC (US); Kirk Francis, Cary, NC (US); Hee-Sook Song, Raleigh, NC (US)

(73) Assignee: BASF Plant Science Company GmbH, Ludwigshafen (DE)

( * ) Notice: Subject to any disclaimer, the term of this patent is extended or adjusted under 35 U.S.C. 154(b) by 408 days.

(21) Appl. No.: 13/383,112

(22) PCT Filed: Jul. 6, 2010

(86) PCT No.: PCT/EP2010/059630
§ 371 (c)(1),
(2), (4) Date: Jan. 9, 2012

(87) PCT Pub. No.: WO2011/003901
PCT Pub. Date: Jan. 13, 2011

(65) Prior Publication Data
US 2012/0117688 A1    May 10, 2012

Related U.S. Application Data

(60) Provisional application No. 61/227,457, filed on Jul. 22, 2009.

(30) Foreign Application Priority Data

Jul. 10, 2009   (EP) ................................... 09009060

(51) Int. Cl.
| | | |
|---|---|---|
| *C12N 15/00* | (2006.01) | |
| *C12N 5/10* | (2006.01) | |
| *C12N 15/82* | (2006.01) | |
| *A01H 5/00* | (2006.01) | |
| *C07H 21/04* | (2006.01) | |
| *C07K 14/415* | (2006.01) | |

(52) U.S. Cl.
CPC .......... *C07K 14/415* (2013.01); *C12N 15/8234* (2013.01)
USPC ........ 800/287; 435/419; 435/468; 435/320.1; 536/24.1; 800/298; 800/278

(58) Field of Classification Search
None
See application file for complete search history.

(56) References Cited

U.S. PATENT DOCUMENTS 5,504,200 A   4/1996   Hall et al.
5,608,152 A   3/1997   Kridl et al.

FOREIGN PATENT DOCUMENTS

| WO | WO2010/069950 A1 | 6/2010 |
| WO | WO2010/118477 A1 | 10/2010 |
| WO | WO2010/122110 A1 | 10/2010 |
| WO | WO2010/129999 A1 | 11/2010 |
| WO | WO2011/067712 A1 | 6/2011 |

OTHER PUBLICATIONS

Dolferus_Plant Phys_105_1075_1994.*
Donald_EMBO J_9_1717_1990.*
Kim_Plant Mol Biol_24_105_1994.*
Potenza_In Vitro Cell Dev Biol Plant_40_1_2004.*
Meinkoth Wahl_Anal Biochem_138_267_1984.*
International Preliminary Report on Patentability for International Application PCT/EP2010/059630, dated Jan. 10, 2012.
Chen, Z.-L., et al., "Regulated Expression of Genes Encoding Soybean β-Conglycinins in Transgenic Plants", Developmental Genetics, 1989, vol. 10, pp. 112-122.
Keddie, J.S., et al., "Cloning and Characterisation of an Oleosin Gene from *Brassica napus*", Plant Molecular Biology, 1992, vol. 19, pp. 443-453.
Sjodahl, S. et al., "Deletion Analysis of the *Brassica napus* Cruciferin Gene *cru 1* Promoter in Transformed Tobacco: Promoter Activity During Early and Late Stages of Embryogenesis is Influenced by *cis*-acting Elements in Partially Separate Regions", Planta, 1995, vol. 197, pp. 264-271.
Reidt, W., et al., "Gene Regulation During Late Embryogenesis: the RY Motif of Maturation-Specific Gene Promoters is a Direct Target of the FUS3 Gene Product", The Plant Journal, 2000, vol. 21, No. 5, pp. 401-408.
Van Der Geest, A.H.M., et al., "Cell Ablation Reveals that Expression from the Phaseolin Promoter is Confined to Embryogenesis and Microsporogenesis¹", Plant Physiol., 1995, vol. 109, pp. 1151-1158.
"MZCCS20014H05.g Maize Endosperm cDNA Library *Zea mays* cDNA, mRNA sequence", EMBL Database, Accession No. CO458784.1, Jun. 8, 2005.
"OG3CF80TV ZM_0._1.5_KB *Zea mays* genomic clone ZMMBMa0774M16, genomic survey sequence", EMBL Database, Accession No. CG290431.1, Aug. 25, 2003.
"*Zea mays* full-length cDNA clone ZM_BFb0116M04 mRNA, complete cds", EMBL Database, Accession No. BT061157.1, Feb. 21, 2009.

* cited by examiner

*Primary Examiner* — Medina A Ibrahim
*Assistant Examiner* — Russell Boggs
(74) *Attorney, Agent, or Firm* — Drinker Biddle & Reath LLP

(57) ABSTRACT

The present invention relates to an expression cassette for regulating seed-specific expression of a polynucleotide of interest, said expression cassette comprising a transcription regulating nucleotide sequence, to a vector comprising said expression cassette, host cells and transgenic plants comprising the expression cassette, and methods of producing said transgenic plants.

12 Claims, 3 Drawing Sheets q-RT-PCR results of MAWS21 showing whole seed and endosperm-specific expression

Diagram of RTP1054

GUS expression in different tissues at different developmental stages driven by p-MAWS21 in transgenic maize with RTP1054

SEQUENCE LISTING

```
<160> NUMBER OF SEQ ID NOS: 28

<210> SEQ ID NO 1
<211> LENGTH: 845
<212> TYPE: DNA
<213> ORGANISM: Zea mays

<400> SEQUENCE: 1
tttactaaat cacgataaat aaaaaagaat ggatgtagta tatgtttgag gccacatatt      60
atatgaaata agtgaatgct cgtgaatgcg gcatagcgga gactgcaggg acgaggacgc     120
cacaagcttc cttcccgtgt gcctgtggac tgtgtggtga agccagggga gtcacaacag     180
gaaacctcca gaaatccgac ggccatgaag gtttctagag ccgccgccgc cgccgccgcc     240
ggatgttaac attaatttca agcagtcaaa agttgaattg tataacggct gattccgcgc     300
gccggacata atattaactt tcgacggact ggcgaaagtt ttagatccat ttctctctat     360
ataattttga tataaattaa gtttatcatg atctgatgag atgacaaatg aaaccacgcg     420
ctgacgcgga tgattatcta gctaggagag agtttctttt ttgtttttgt ttttgtttc     480 tcccagtcat ggtggaaata aaggcgaatt cttatccagc aggtatattt gttttttccc     540
```

-continued

```
cacactgcaa tggtggaaag gcgagttctt atccagcagc tagcgcgcca tggtggaaag      600
gcgtatcatt atcctaccct gctgccgatg aacttgtgtt ctttcttctc aaactttcgt      660
tcttttccta ttttctttat cctgccctgc gcacacgaaa catgctaatt aaagacgtac      720
gcgatgcgtc ctaagcttct ccactaataa tataaccccg agcatgcacg cacgctgatc      780
atccatctat aaatacgcca attagcaaac tagagctact agcagcaggc caatggagaa      840
ccctc                                                                  845
```

```
<210> SEQ ID NO 2
<211> LENGTH: 948
<212> TYPE: DNA
<213> ORGANISM: Zea mays
<220> FEATURE:
<221> NAME/KEY: CDS
<222> LOCATION: (1)..(948)

<400> SEQUENCE: 2
```

| | | | | | | | | | | | | | | | | |
|---|---|---|---|---|---|---|---|---|---|---|---|---|---|---|---|---|
| atg | gct | ccg | gcc | atg | tcg | gcg | cag | ttc | aca | aga | ata | acc | ttc | agc | aac | 48 |
| Met | Ala | Pro | Ala | Met | Ser | Ala | Gln | Phe | Thr | Arg | Ile | Thr | Phe | Ser | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | ttt | gtc | cgt | cgg | gct | ggc | cca | ggc | agc | acg | gag | ctg | acc | gtg | gag | 96 |
| Leu | Phe | Val | Arg | Arg | Ala | Gly | Pro | Gly | Ser | Thr | Glu | Leu | Thr | Val | Glu | |
| | | 20 | | | | | 25 | | | | | 30 | | | | |

| | | | | | | | | | | | | | | | | |
|---|---|---|---|---|---|---|---|---|---|---|---|---|---|---|---|---|
| gga | agg | cca | tcc | gac | cag | ctg | ggc | agg | aga | aac | ctc | act | gac | agc | ccc | 144 |
| Gly | Arg | Pro | Ser | Asp | Gln | Leu | Gly | Arg | Arg | Asn | Leu | Thr | Asp | Ser | Pro | |
| | | | 35 | | | | | 40 | | | | | 45 | | | |

| | | | | | | | | | | | | | | | | |
|---|---|---|---|---|---|---|---|---|---|---|---|---|---|---|---|---|
| gta | ttt | gac | ggc | cgt | ggc | cct | gac | gcc | agc | ctc | gtg | gct | cgc | gta | cag | 192 |
| Val | Phe | Asp | Gly | Arg | Gly | Pro | Asp | Ala | Ser | Leu | Val | Ala | Arg | Val | Gln | |
| 50 | | | | | 55 | | | | | 60 | | | | | | |

| | | | | | | | | | | | | | | | | |
|---|---|---|---|---|---|---|---|---|---|---|---|---|---|---|---|---|
| gga | gtc | gct | acc | cag | atg | ggc | gac | gtg | cgc | cag | ttg | tac | acc | gtc | gtg | 240 |
| Gly | Val | Ala | Thr | Gln | Met | Gly | Asp | Val | Arg | Gln | Leu | Tyr | Thr | Val | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | cag | gag | agg | ccg | ctc | aag | ggc | tcc | acg | ctc | gtc | acc | gaa | ggc | gcg | 288 |
| Phe | Gln | Glu | Arg | Pro | Leu | Lys | Gly | Ser | Thr | Leu | Val | Thr | Glu | Gly | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | aca | gaa | ggg | tca | gac | gag | tgg | gcg | acc | tac | ggt | gga | act | gga | gtg | 336 |
| Met | Thr | Glu | Gly | Ser | Asp | Glu | Trp | Ala | Thr | Tyr | Gly | Gly | Thr | Gly | Val | |
| | | | | 100 | | | | | 105 | | | | | 110 | | |

| | | | | | | | | | | | | | | | | |
|---|---|---|---|---|---|---|---|---|---|---|---|---|---|---|---|---|
| ttc | gcg | atg | gcg | aga | ggc | gta | ata | agg | aga | acg | ttt | ctt | gcc | gac | acg | 384 |
| Phe | Ala | Met | Ala | Arg | Gly | Val | Ile | Arg | Arg | Thr | Phe | Leu | Ala | Asp | Thr | |
| | | | 115 | | | | | 120 | | | | | 125 | | | |

| | | | | | | | | | | | | | | | | |
|---|---|---|---|---|---|---|---|---|---|---|---|---|---|---|---|---|
| agc | ggc | ggg | aac | tcc | gac | gag | ctt | gcc | gtg | gag | gtt | ctc | tgc | ccg | gtg | 432 |
| Ser | Gly | Gly | Asn | Ser | Asp | Glu | Leu | Ala | Val | Glu | Val | Leu | Cys | Pro | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| ttc | cgc | ccg | gcg | gcg | ttt | ggc | tca | tcg | tcg | tca | cag | cca | gca | gca | aag | 480 |
| Phe | Arg | Pro | Ala | Ala | Phe | Gly | Ser | Ser | Ser | Ser | Gln | Pro | Ala | Ala | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gac | atc | agc | tcc | acc | gtc | gtc | gtc | acc | aag | gtc | gga | gtg | tgg | ggt | gga | 528 |
| Asp | Ile | Ser | Ser | Thr | Val | Val | Val | Thr | Lys | Val | Gly | Val | Trp | Gly | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | gga | ggg | tcg | gcg | cag | gac | atc | gcg | acg | acg | gag | ccg | ccg | agg | cgt | 576 |
| Glu | Gly | Gly | Ser | Ala | Gln | Asp | Ile | Ala | Thr | Thr | Glu | Pro | Pro | Arg | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| ctg | cag | agc | ctg | acc | gtc | cgc | gcc | ggc | gtt | gcc | gtg | gac | tcc | atc | gag | 624 |
| Leu | Gln | Ser | Leu | Thr | Val | Arg | Ala | Gly | Val | Ala | Val | Asp | Ser | Ile | Glu | |
| | | | | 195 | | | | | 200 | | | | | 205 | | |

| | | | | | | | | | | | | | | | | |
|---|---|---|---|---|---|---|---|---|---|---|---|---|---|---|---|---|
| ttc | acc | tac | agt | acc | gac | aca | ggt | ggt | cag | acg | cgc | acc | gct | ggg | cga | 672 |
| Phe | Thr | Tyr | Ser | Thr | Asp | Thr | Gly | Gly | Gln | Thr | Arg | Thr | Ala | Gly | Arg | |
| | 210 | | | | | 215 | | | | | 220 | | | | | |

```
tgg ggt gga ctt ggc ggc aac gtc cgg aag ctc gat ctt ggc gac gct      720
Trp Gly Gly Leu Gly Gly Asn Val Arg Lys Leu Asp Leu Gly Asp Ala
225                 230                 235                 240 gaa tac gtc aag gaa gtt tct gga acg tac ggc gca ttc gaa ggt gcg      768
Glu Tyr Val Lys Glu Val Ser Gly Thr Tyr Gly Ala Phe Glu Gly Ala
                245                 250                 255 act acc ctt acc tcg ttc agg att gtc acc agc acc gcc aga gct tgg      816
Thr Thr Leu Thr Ser Phe Arg Ile Val Thr Ser Thr Ala Arg Ala Trp
                260                 265                 270 ggg cca tgg ggc atc gag agc ggc aca cgt ttc tgc atc acc gcg ccc      864
Gly Pro Trp Gly Ile Glu Ser Gly Thr Arg Phe Cys Ile Thr Ala Pro
        275                 280                 285 atc ggc agc agc atc gtg gga ttc tat gga cgc gcg acg acc agg ctc      912
Ile Gly Ser Ser Ile Val Gly Phe Tyr Gly Arg Ala Thr Thr Arg Leu
        290                 295                 300 gtc gct gcg atc ggt gtc tac ctg cgc caa ctt tag                      948
Val Ala Ala Ile Gly Val Tyr Leu Arg Gln Leu
305                 310                 315

<210> SEQ ID NO 3
<211> LENGTH: 315
<212> TYPE: PRT
<213> ORGANISM: Zea mays

<400> SEQUENCE: 3

Met Ala Pro Ala Met Ser Ala Gln Phe Thr Arg Ile Thr Phe Ser Asn
1               5                   10                  15

Leu Phe Val Arg Arg Ala Gly Pro Gly Ser Thr Glu Leu Thr Val Glu
            20                  25                  30

Gly Arg Pro Ser Asp Gln Leu Gly Arg Arg Asn Leu Thr Asp Ser Pro
        35                  40                  45

Val Phe Asp Gly Arg Gly Pro Asp Ala Ser Leu Val Ala Arg Val Gln
    50                  55                  60

Gly Val Ala Thr Gln Met Gly Asp Val Arg Gln Leu Tyr Thr Val Val
65                  70                  75                  80

Phe Gln Glu Arg Pro Leu Lys Gly Ser Thr Leu Val Thr Glu Gly Ala
                85                  90                  95

Met Thr Glu Gly Ser Asp Glu Trp Ala Thr Tyr Gly Gly Thr Gly Val
            100                 105                 110

Phe Ala Met Ala Arg Gly Val Ile Arg Arg Thr Phe Leu Ala Asp Thr
        115                 120                 125

Ser Gly Gly Asn Ser Asp Glu Leu Ala Val Glu Val Leu Cys Pro Val
    130                 135                 140

Phe Arg Pro Ala Ala Phe Gly Ser Ser Ser Gln Pro Ala Ala Lys
145                 150                 155                 160

Asp Ile Ser Ser Thr Val Val Thr Lys Val Gly Val Trp Gly Gly
                165                 170                 175

Glu Gly Gly Ser Ala Gln Asp Ile Ala Thr Thr Glu Pro Pro Arg Arg
            180                 185                 190

Leu Gln Ser Leu Thr Val Arg Ala Gly Val Ala Val Asp Ser Ile Glu
        195                 200                 205

Phe Thr Tyr Ser Thr Asp Thr Gly Gly Gln Thr Arg Thr Ala Gly Arg
    210                 215                 220

Trp Gly Gly Leu Gly Gly Asn Val Arg Lys Leu Asp Leu Gly Asp Ala
225                 230                 235                 240

Glu Tyr Val Lys Glu Val Ser Gly Thr Tyr Gly Ala Phe Glu Gly Ala
                245                 250                 255
```

Thr Thr Leu Thr Ser Phe Arg Ile Val Thr Ser Thr Ala Arg Ala Trp
        260                 265                 270

Gly Pro Trp Gly Ile Glu Ser Gly Thr Arg Phe Cys Ile Thr Ala Pro
    275                 280                 285

Ile Gly Ser Ser Ile Val Gly Phe Tyr Gly Arg Ala Thr Thr Arg Leu
290                 295                 300

Val Ala Ala Ile Gly Val Tyr Leu Arg Gln Leu
305                 310                 315

<210> SEQ ID NO 4
<211> LENGTH: 1131
<212> TYPE: DNA
<213> ORGANISM: Zea mays

<400> SEQUENCE: 4

```
cgagcatcct agtgactccc atggctccgg ccatgtcggc gcagttcaca agaataacct      60
tcagcaacct gtttgtccgt cgggctggcc caggcagcac ggagctgacc gtggagggaa     120
ggccatccga ccagctgggc aggagaaacc tcactgacag ccccgtattt gacggccgtg     180
gccctgacgc cagcctcgtg gctcgcgtac agggagtcgc tacccagatg ggcgacgtgc     240
gccagttgta caccgtcgtg ttccaggaga ggccgctcaa gggctccacg ctcgtcaccg     300
aaggcgcgat gacagaaggg tcagacgagt gggcgaccta cggtggaact ggagtgttcg     360
cgatggcgag aggcgtcata aggagaacgt tcttgccga cacgagcggc gggaactccg     420
acgagcttgc cgtggaggtt ctctgcccgg tgttccgccc ggcggcgttt ggctcatcgt     480
cgtcacagcc agcagcaaag gacatcagct ccaccgtcgt cgtcaccaag gtcggagtgt     540
ggggtggaga gggagggtcg gcgcaggaca tcgcgacgac ggagccgccg aggcgtctgc     600
agagcctgac cgtccgcgcc ggcgttgccg tggactccat cgagttcacc tacagtaccg     660
acacaggtgg tcagacgcgc accgctgggc gatggggtgg acttggcggc aacgtccgga     720
agctcgatct tggcgacgct gaatacgtca aggaagtttc tggaacgtac ggcgcattcg     780
aaggtgcgac taccttacc tcgttcagga ttgtcaccag caccgccaga gcttgggggc     840
catggggcat cgagagcggc acacgtttct gcatcaccgc gcccatcggc agcagcatcg     900
tgggattcta tggacgcgcg acgaccaggc tcgtcgctgc gatcggtgtc tacctgcgcc     960
aactttagtc tggtttcagc agcaggacgg gtactacaga tatgctagat aaaggtctta    1020
tatatgtcat atgacctatc atggtcttat atgttcgatc gtcgtcgtgt ctgtatgtac    1080
atacatggtt gtcaaataaa gctctttgca ttttgataaa aaaaaaaaa a              1131
```

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggccatgtcg gcgcagttca ca                                                22

<210> SEQ ID NO 6
<211> LENGTH: 22
<212> TYPE: DNA
<213> ORGANISM: Artificial Sequence
<220> FEATURE:
<223> OTHER INFORMATION: Primer

```
<400> SEQUENCE: 6
cagggccacg gccgtcaaat ac                                               22

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
gtgtggggtg gagagggagg gtc                                              23

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
cgcgtctgac cacctgtgtc ggta                                             24

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gtaaagttct tcctgatctg aat                                              23

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tcggaagcag ccttaata                                                    18

<210> SEQ ID NO 11
<211> LENGTH: 24
<212> TYPE: DNA
<213> ORGANISM: Artificial Sequence
<220> FEATURE:
<223> OTHER INFORMATION: Promoter primer forward

<400> SEQUENCE: 11
tttactaaat cacgataaat aaaa                                             24

<210> SEQ ID NO 12
<211> LENGTH: 20
<212> TYPE: DNA
<213> ORGANISM: Artificial Sequence
<220> FEATURE:
<223> OTHER INFORMATION: Promoter promer reverse

<400> SEQUENCE: 12
gagggttctc cattggcctg                                                  20

<210> SEQ ID NO 13
<211> LENGTH: 2192
```

<212> TYPE: DNA
<213> ORGANISM: Zea mays

<400> SEQUENCE: 13

```
tttactaaat cacgataaat aaaaaagaat ggatgtagta tattgtttga ggccacatat      60
tatatgaaat aagtgaatgc tcgtgaatgc ggcatagcgg agactgcagg gacgaggacg     120
ccacaagctt ccttcccgtg tgcctgtgga ctgtgtggtg aagccagggg agtcacaaca     180
ggaaacctcc agaaatccga cggccatgaa ggtttctaga gccgccgccg ccgccgccgc     240
cggatgttaa cattaatttc aagcagtcaa aagttgaatt gtataacggc tgattccgcg     300
cgccggacat aatattaact ttcgacggac tggcgaaagt tttagatcca tttctctcta     360
tataattttg atataaatta agtttatcat gatctgatga gatgacaaat gaaaccacgc     420
gctgacgcgg atgattatct agctaggaga gagtttcttt tttgtttttg ttttttgttt     480
ctcccagtca tggtggaaat aaaggcgaat tcttatccag caggtatatt tgttttttcc     540
ccacactgca atggtggaaa ggcgagttct tatccagcag ctagcgcgcc atggtggaaa     600
ggcgtatcat tatcctaccc tgctgccgat gaacttgtgt tctttcttct caaactttcg     660
ttcttttcct attttcttta tcctgccctg cgcacacgaa acatgctaat taaagacgta     720
cgcgatgcgt cctaagcttc tccactaata atataacccc gagcatgcac gcacgctgat     780
catccatcta taaatacgcc aattagcaaa ctagagctac tagcagcagg ccaatggaga     840
accctccgag catcctagtg actcccatgg ctccggccat gtcggcgcag ttcacaagaa     900
taaccttcag caacctgttt gtccgtcggg ctggcccagg cagcacggag ctgaccgtgg     960
agggaaggcc atccgaccag ctgggcagga gaaacctcac tgacagcccc gtatttgacg    1020
gccgtggccc tgacgccagc ctcgtggctc gcgtacaggg agtcgctacc cagatgggcg    1080
acgtgcgcca gttgtacacc gtcgtgttcc aggagaggta tatctgtaca tgtgtatatg    1140
ctcaggcttc ttgtgtgtac actatggttt tatgctgttg atttcattca tgcatgcgtg    1200
catatcgtca ggccgctcaa gggctccacg ctcgtcaccg aaggcgcgat gacagaaggg    1260
tcagacgagt gggcgatcta cggtggaact ggagtgttcg cgatggcgag aggcgtcata    1320
aggagaacgt ttcttgccga cacgagcggc gggaactccg acgagcttgc cgtggaggtt    1380
ctctgcccgg tgttccgccc ggcggcgttt ggctcatcgt cgtcacagcc agcagcaaag    1440
gtgagagcga gcgagcgagc gagcgagaaa ccgtttctcc ttcttactca tcatatcatc    1500
cgatgaacaa cactgggatg gatggatgga tggatgcagg acatcagctc caccgtcgtc    1560
gtcaccaagg tcggagtgtg gggtggagag ggagggtcgg cgcaggacat cgcgacgacg    1620
gagccgccga ggcgtctgca gagcctgacc gtccgcgccg gcgttgccgt ggactccatc    1680
gagttcacct acagtaccga cacaggtggt cagacgcgca ccgctgggcg atggggtgga    1740
cttggcggca acgtccggaa ggtgagtgat ctgatcgggt ttccgtgtac ggttccatca    1800
acggcgtctc tagctatgaa cttgtgcagc agggacgacg atagagaact actgatgaac    1860
atatatatat atgagcacaa acatgcgtgc gtgcgtgcag ctcgatcttg gcgacgctga    1920
atacgtcaag gaagtttctg gaacgtacgg cgcattcgaa ggtgcgacta cccttacctc    1980
gttcaggatt gtcaccagca ccgccagagc ttggggggcca tggggcatcg agagcggcac    2040
acgtttctgc atcaccgcgc ccatcggcag cagcatcgtg ggattctatg gacgcgcgac    2100
gaccaggctc gtcgctgcga tcggtgtcta cctgcgccaa ctttagtctg gtttcagcag    2160
caggacgggt actacagata tgctagataa ag                                  2192
```

```
<210> SEQ ID NO 14
<211> LENGTH: 13
<212> TYPE: DNA
<213> ORGANISM: Zea mays

<400> SEQUENCE: 14
tttgaggcca cat                                                        13

<210> SEQ ID NO 15
<211> LENGTH: 13
<212> TYPE: DNA
<213> ORGANISM: Zea mays

<400> SEQUENCE: 15
gaggacgcca caa                                                        13

<210> SEQ ID NO 16
<211> LENGTH: 15
<212> TYPE: DNA
<213> ORGANISM: Zea mays

<400> SEQUENCE: 16
tgtgactccc ctggc                                                      15

<210> SEQ ID NO 17
<211> LENGTH: 15
<212> TYPE: DNA
<213> ORGANISM: Zea mays

<400> SEQUENCE: 17
catgaaggtt tctag                                                      15

<210> SEQ ID NO 18
<211> LENGTH: 15
<212> TYPE: DNA
<213> ORGANISM: Zea mays

<400> SEQUENCE: 18
ctagaaacct tcatg                                                      15

<210> SEQ ID NO 19
<211> LENGTH: 15
<212> TYPE: DNA
<213> ORGANISM: Zea mays

<400> SEQUENCE: 19
tttgactgct tgaaa                                                      15

<210> SEQ ID NO 20
<211> LENGTH: 13
<212> TYPE: DNA
<213> ORGANISM: Zea mays

<400> SEQUENCE: 20
cgcgctgacg cgg                                                        13

<210> SEQ ID NO 21
<211> LENGTH: 15
<212> TYPE: DNA
<213> ORGANISM: Zea mays

<400> SEQUENCE: 21
catgactggg agaaa                                                      15
```

```
<210> SEQ ID NO 22
<211> LENGTH: 10
<212> TYPE: DNA
<213> ORGANISM: Zea mays

<400> SEQUENCE: 22
caagttcatc                                                           10

<210> SEQ ID NO 23
<211> LENGTH: 11
<212> TYPE: DNA
<213> ORGANISM: Zea mays

<400> SEQUENCE: 23
agcatgcacg c                                                         11

<210> SEQ ID NO 24
<211> LENGTH: 10
<212> TYPE: DNA
<213> ORGANISM: Zea mays

<400> SEQUENCE: 24
ctataaatac                                                           10

<210> SEQ ID NO 25
<211> LENGTH: 3826
<212> TYPE: DNA
<213> ORGANISM: Artificial Sequence
<220> FEATURE:
<223> OTHER INFORMATION: Binary Vector

<400> SEQUENCE: 25
ttttactaaa tcacgataaa taaaaagaa tggatgtagt atatgtttga ggccacatat      60
tatatgaaat aagtgaatgc tcgtgaatgc ggcatagcgg agactgcagg gacgaggacg    120
ccacaagctt ccttcccgtg tgcctgtgga ctgtgtggtg aagccagggg agtcacaaca    180
ggaaacctcc agaaatccga cggccatgaa ggtttctaga gccgccgccg ccgccgccgc    240
cggatgttaa cattaatttc aagcagtcaa agttgaattt gtataacggc tgattccgcg    300
cgccggacat aatattaact ttcgacggac tggcgaaagt tttagatcca tttctctcta    360
tataattttg atataaatta agtttatcat gatctgatga gatgacaaat gaaaccacgc    420
gctgacgcgg atgattatct agctaggaga gagtttcttt tttgtttttg tttttttgttt  480 ctcccagtca tggtggaaat aaaggcgaat tcttatccag caggtatatt tgttttttcc    540
ccacactgca atggtggaaa ggcgagttct tatccagcag ctagcgcgcc atggtggaaa    600
ggcgtatcat tatcctaccc tgctgccgat gaacttgtgt tctttcttct caaactttcg    660 ttctttttcct attttctttta tcctgccctg cgcacacgaa acatgctaat taaagacgta    720
cgcgatgcgt cctaagcttc tccactaata atataaccc gagcatgcac gcacgctgat    780
catccatcta taaatacgcc aattagcaaa ctagagctac tagcagcagg ccaatggaga    840
accctccgag catcctagtg actcccacgt acggcctagg ccttcacctg cggagggtaa    900
gatccgatca ccatcttctg aatttctgtt cttgatctgt catgtataat aactgtctag    960
tcttggtgtt ggtgagatgg aaattcggtg gatctcggaa gggatattgt tcgtttgctg   1020
gggttttttt tgtgtgttgt gatccgtaga gaatttgtgt ttatccatgt tgttgatctt   1080
ggtatgtatt catgacatat tgacatgcat gtgttgtatg tgtcatatgt gtgcctctcc   1140
```

```
ttgggatttg ttttggataa tagaacatgt tatggactca atagtctgtg aacaaatctt    1200
tttttagatg gtggccaaat ctgatgatga tctttcttga gaggaaaaag ttcatgatag    1260
aaaaatcttt tttgagatgg tggcttaatg tgatgatgat ctttcttgag aggaaaaaaa    1320
agattcatta taggagattt tgatttagct cctttccacc gatattaaat gaggagcatg    1380
catgctgatt gctgataagg atctgatttt tttatcccct cttctttgaa cagacaagaa    1440
ataggctctg aatttctgat tgattatttg tacatgcaga agggcgaatt cgacctaggc    1500
caagtttgta caaaaaagca ggcttgataa ccaaccatgg tccgtcctgt agaaacccca    1560
acccgtgaaa tcaaaaaact cgacggcctg tgggcattca gtctggatcg cgaaaactgt    1620
ggaattgatc agcgttggtg ggaaagcgcg ttacaagaaa gccgggcaat tgctgtgcca    1680
ggcagtttta cgatcagtt cgccgatgca gatattcgta attatgcggg caacgtctgg    1740
tatcagcgcg aagtctttat accgaaaggt tgggcaggcc agcgtatcgt gctgcgtttc    1800
gatgcggtca ctcattacgg caaagtgtgg gtcaataatc aggaagtgat ggagcatcag    1860
ggcggctata cgccatttga agccgatgtc acgccgtatg ttattgccgg gaaaagtgta    1920
cgtaagtttc tgcttctacc tttgatatat ataataat tatcattaat tagtagtaat    1980
ataatatttc aaatatttt ttcaaaataa agaatgtag tatatagcaa ttgcttttct    2040
gtagtttata agtgtgtata ttttaattta taacttttct aatatatgac caaaatttgt    2100
tgatgtgcag gtatcaccgt ttgtgtgaac aacgaactga actggcagac tatcccgccg    2160
ggaatggtga ttaccgacga aaacggcaag aaaaagcagt cttacttcca tgatttcttt    2220
aactatgccg gaatccatcg cagcgtaatg ctctacacca cgccgaacac ctgggtggac    2280
gatatcaccg tggtgacgca tgtcgcgcaa gactgtaacc acgcgtctgt tgactggcag    2340
gtggtggcca atggtgatgt cagcgttgaa ctgcgtgatg cggatcaaca ggtggttgca    2400
actggacaag gcactagcgg gactttgcaa gtggtgaatc cgcacctctg caaccgggt    2460 gaaggttatc tctatgaact gtgcgtcaca gccaaaagcc agacagagtg tgatatctac    2520
ccgcttcgcg tcggcatccg gtcagtggca gtgaagggcg aacagttcct gattaaccac    2580
aaaccgttct actttactgg ctttggtcgt catgaagatg cggacttgcg tggcaaagga    2640
ttcgataacg tgctgatggt gcacgaccac gcattaatgg actggattgg ggccaactcc    2700
taccgtacct cgcattaccc ttacgctgaa gagatgctcg actgggcaga tgaacatggc    2760
atcgtggtga ttgatgaaac tgctgctgtc ggctttaacc tctctttagg cattggtttc    2820
gaagcgggca caagccgaa agaactgtac agcgaagagg cagtcaacgg ggaaactcag    2880
caagcgcact tacaggcgat taaagagctg atagcgcgtg acaaaaacca cccaagcgtg    2940
gtgatgtgga gtattgccaa cgaaccggat accgtccgc aaggtgcacg ggaatatttc    3000
gcgccactgg cggaagcaac gcgtaaactc gacccgacgc gtccgatcac ctgcgtcaat    3060
gtaatgttct gcgacgctca caccgatacc atcagcgatc tctttgatgt gctgtgcctg    3120
aaccgttatt acggatggta tgtccaaagc ggcgatttgg aaacggcaga aaggtactg    3180 gaaaagaac ttctggcctg gcaggagaaa ctgcatcagc cgattatcat caccgaatac    3240
ggcgtggata cgttagccgg gctgcactca atgtacaccg acatgtggag tgaagagtat    3300
cagtgtgcat ggctggatat gtatcaccgc gtctttgatc gcgtcagcgc cgtcgtcggt    3360
gaacaggtat ggaatttcgc cgattttgcg acctcgcaag gcatattgcg cgttggcggt    3420
aacaagaaag gatcttcac tcgcgaccgc aaaccgaagt cggcggcttt tctgctgcaa    3480
aaacgctgga ctggcatgaa cttcggtgaa aaaccgcagc agggaggcaa acaatgaatc    3540
```

```
aaacccagct tcttgtaca aagtgggacc taggatcgtt caaacatttg gcaataaagt    3600
ttcttaagat tgaatcctgt tgccggtctt gcgatgatta tcatataatt tctgttgaat    3660
tacgttaagc atgtaataat taacatgtaa tgcatgacgt tatttatgag atgggttttt    3720
atgattagag tcccgcaatt atacatttaa tacgcgatag aaaacaaaat atagcgcgca    3780
aactaggata aattatcgcg cgcggtgtca tctatgttac tagatc                  3826

<210> SEQ ID NO 26
<211> LENGTH: 845
<212> TYPE: DNA
<213> ORGANISM: Artificial Sequence
<220> FEATURE:
<223> OTHER INFORMATION: Variant 1

<400> SEQUENCE: 26
tttactaaat cacgataaat aaaaaagaat ggatgtagta tatgtttgag gccacatatt      60
atatgaaata agtgaatgct cgtgaatgcg gcatagcgga gactgcaggg acgaggacgc     120
cacaagcttc cttcccgtgt gcctgtggac tgtgtggtga agccagggga gtcacaacag     180
gaaacctcca gaaatccgac ggccatgaag gtttctagag ccgccgccgc cgccgccgcc     240
ggatgttaac attaatttca agcagtcaaa agttgaattg tataacggct gattccgcgc     300
gccggacata atattaactt tcgacggact ggcgaaagtt ttagatccat ttctctctat     360
ataattttga tataaattaa gtttatcatg atctgatgag atgacaaatg aaaccacgcg     420
ctgacgcgga tgattatcta gctaggagag agtttctttt ttgtttttgt tttttgtttc     480
tcccagtcat ggtggaaata aaggcgaatt cttatccagc aggtatattt gttttttccc     540
cacactgcaa tggtggaaag gcgagttctt atccagcagc tagcgcgcca tggtggaaag     600
gcgtatcatt atcctaccct gctgccgatg aacttgtgtt ctttcttctc aaactttcgt     660
tcttttccta ttttctttat cctgccctgc gcacacgaaa catgctaatt aaagacgtac     720
gcgatgcgtc ctaagcttct ccactaataa tataaccccg agcatgcacg cacgctgatc     780
atccatctat aaatacgcca attagcaaac tagagctact agcagcaggc caatggagaa     840
ccctc                                                                 845

<210> SEQ ID NO 27
<211> LENGTH: 845
<212> TYPE: DNA
<213> ORGANISM: Artificial Sequence
<220> FEATURE:
<223> OTHER INFORMATION: Variant 2

<400> SEQUENCE: 27
tttactaaat cacgataaat aaaaaagabv hgbvhtagta tbvhtttgag gccacatatt      60
atbvhaaata agtgabvhct cgtgabvhcg gcatagcgga gactgcaggg acgaggacgc     120
cacaagcttc cttcccgtgt gcctgtggac tgtgtggtga agccagggga gtcacaacag     180
gaaacctcca gaaatccgac ggccbvhaag gtttctagag ccgccgccgc cgccgccgcc     240
ggbvhttaac attaatttca agcagtcaaa agttgaattg tataacggct gattccgcgc     300
gccggacata atattaactt tcgacggact ggcgaaagtt ttagatccat ttctctctat     360
ataattttga tataaattaa gtttatcbvh atctgbvhag bvhacaabvh aaaccacgcg     420
ctgacgcggb vhattatcta gctaggagag agtttctttt ttgtttttgt tttttgtttc     480
tcccagtcbv hgtggaaata aaggcgaatt cttatccagc aggtatattt gttttttccc     540
```

```
cacactgcab vhgtggaaag gcgagttctt atccagcagc tagcgcgccb vhgtggaaag    600
gcgtatcatt atcctaccct gctgccgbvh aacttgtgtt ctttcttctc aaactttcgt    660
tcttttccta ttttctttat cctgccctgc gcacacgaaa cbvhctaatt aaagacgtac    720
gcgbvhcgtc ctaagcttct ccactaataa tataaccccg agcbvhcacg cacgctgatc    780
atccatctat aaatacgcca attagcaaac tagagctact agcagcaggc cabvhgagaa    840
ccctc                                                                845

<210> SEQ ID NO 28
<211> LENGTH: 845
<212> TYPE: DNA
<213> ORGANISM: Artificial Sequence
<220> FEATURE:
<223> OTHER INFORMATION: Variant 3

<400> SEQUENCE: 28
tttactaaat cacgataaat aaaaaagabv hgbvhtagta rbvhtttgag gccacatart     60
arbvhaaata agtgabvhct cgtgabvhcg gcatagcgga gactgraggg acgaggacgc    120
cacaagcttc cttcccgtgt grctgtggac tgtgtggtga agccagggga gtracaacag    180
gaaacctrra gaaatccgac ggccbvhaag gtttctagag ccgccgccgc cgccgccgcc    240
ggbvhttaac atraatttra agcagtraaa agttgaattg tataacggct gattccgcgc    300
gccggacata atartaactt tcgacggact ggcgaaagtt ttagatccat ttctctctar    360
ataattttga tataaattaa gtttarcbvh atctgbvhag bvhacaabvh aaaccacgcg    420
ctgacgcggb vhattatcta gctaggagag agtttctttt ttgtttttgt tttttgtttr    480
rcccagtcbv hgtggaaata aaggcgaatt cttarccagc aggtarattt gttttttccc    540
cacactgcab vhgtggaaag gcgagttctt arccagcagc tagcgcgccb vhgtggaaag    600
gcgtatratt arcctarcct gctgccgbvh aacttgtgtt ctttcttctc aaactttcgt    660
tcttttccta rtttctttar cctgccctgc gcacacgaaa cbvhctaatt aaagacgtar    720
gcgbvhcgtc ctaagcttct ccactaataa tataaccccg agcbvhcacg cacgctgatr    780
atccatctat aaatargcca attagcaaac tagagctart agcagcaggc cabvhgagaa    840
ccctc                                                                845
```

EXPRESSION CASSETTES FOR ENDOSPERM-SPECIFIC EXPRESSION IN PLANTS

RELATED APPLICATIONS

This application is a national stage application (under 35 U.S.C. §371) of PCT/EP2010/059630, filed Jul. 6, 2010 which claims benefit of European Application No. 09009060.6 filed Jul. 10, 2009 and U.S. Provisional Application No. 61/227,457, filed Jul. 22, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00165_US. The size of the text file is 25 KB and the text file was created on Jan. 4, 2012.

FIELD OF THE INVENTION

The present invention relates to expression cassettes comprising transcription regulating nucleotide sequences with seed-preferential or seed-specific expression profiles in plants obtainable from the *Zea mays*. The transcription regulating nucleotide sequences preferably exhibit strong expression activity especially in whole seeds and, particularly, in the endosperm.

BACKGROUND OF THE INVENTION

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

The seed-preferential or seed-specific promoters are useful for expressing genes as well as for producing large quantities of protein, for expressing oils or proteins of interest, e.g., antibodies, genes for increasing the nutritional value of the seed and the like. It is advantageous to have the choice of a variety of different promoters so that the most suitable promoter may be selected for a particular gene, construct, cell, tissue, plant or environment. Moreover, the increasing interest in cotransforming plants with multiple plant transcription units (PTU) and the potential problems associated with using common regulatory sequences for these purposes merit having a variety of promoter sequences available.

Only a few seed-specific promoters have been cloned and studied in detail; these include promoters for seed storage protein genes, such as a phaseolin promoter (U.S. Pat. No. 5,504,200) and a napin promoter (U.S. Pat. No. 5,608,152). Storage proteins are usually present in large amounts, making it relatively easy to isolate storage protein genes and the gene promoters. Even so, the number of available seed specific promoters is still limited. Furthermore, most of these promoters suffer from several drawbacks; they have a limited period of time during seed development in which they are active, and they may be expressed in other tissues as well. For example, storage protein gene promoters are expressed mainly in the mid to late embryo development stage (Chen et al., Dev. Genet., (2): 112-122 (1989); Keddie et al., Plant Mol. Biol., 19 (3): 443-53 (1992); Sjodahl et al., Planta., 197 (2): 264-71 (1995); Reidt et al., Plant J., 21 (5): 401-8 (2000)), and also may have activity in other tissues, such as pollen, stamen and/or anthers (as, for example, the phaseolin promoter, as reported by Ahm, V, et al. Plant Phys 109: 1151-1158 (1995)).

There is, therefore, a great need in the art for the identification of novel sequences that can be used for expression of selected transgenes in economically important plants. Thus, the problem underlying the present invention is to provide new and alternative expression cassettes for seed-preferential or seed-specific expression of transgenes in plants. The problem is solved by the present invention.

SUMMARY OF THE INVENTION

Accordingly, a first embodiment of the invention relates to an expression cassette for regulating seed-specific expression of a polynucleotide of interest, said expression cassette comprising a transcription regulating nucleotide sequence selected from the group of sequences consisting of:

(a) a nucleic acid sequence of SEQ ID NO: 1, or a variant thereof;
(b) a nucleic acid sequence which is at least 80% identical to a nucleic acid sequence shown in any one of SEQ ID NO: 1;
(c) a nucleic acid sequence which hybridizes under stringent conditions to a nucleic acid sequence of SEQ ID NO: 1, or a variant thereof;
(d) a nucleic acid sequence which hybridizes to a nucleic acid sequence located upstream of an open reading frame sequence of SEQ ID NO: 2, or a variant thereof;
(e) a nucleic acid sequence which hybridizes to a nucleic acid sequences located upstream of an open reading frame sequence encoding an amino acid sequence of SEQ ID NO: 3, or a variant thereof;
(f) a nucleic acid sequence which hybridizes to a nucleic acid sequence located upstream of an open reading frame sequence being at least 80% identical to an open reading frame sequence of SEQ ID NO: 2, wherein the open reading frame encodes a seed protein;
(g) a nucleic acid sequence which hybridizes to a nucleic acid sequences located upstream of an open reading frame encoding an amino acid sequence being at least 80% identical to an amino acid sequence as shown in SEQ ID NO: 3, wherein the open reading frame encodes a seed protein;
(h) a nucleic acid sequence obtainable by 5' genome walking or by thermal asymmetric interlaced polymerase chain reaction (TAIL-PCR) on genomic DNA from the first exon of an open reading frame sequence as shown in SEQ ID NO: 2; and
(i) a nucleic acid sequence obtainable by 5' genome walking or TAIL PCR on genomic DNA from the first exon of an open reading frame sequence being at least 80% identical to an open reading frame as shown in SEQ ID NO: 2, wherein the open reading frame encodes a seed protein; and
(j) a nucleic acid sequence obtainable by 5' genome walking or TAIL PCR on genomic DNA from the first exon of an open reading frame sequence encoding an amino acid sequence being at least 80% identical to an amino acid sequence encoded by an open reading frame as shown in any one of SEQ ID NO: 3, wherein the open reading frame encodes a seed protein.

In a preferred embodiment, the expression cassette further comprises at least one polynucleotide of interest being operatively linked to the transcription regulating nucleotide sequence, preferably being heterologous with respect to the transcription regulating nucleotide sequence.

In another aspect, the present invention refers to a transgenic plant tissue, plant organ, plant or seed comprising the expression cassette or the vector of the present invention. Preferably, the transgenic plant is a monocotyledone.

In another aspect, the present invention refers method for producing a transgenic plant tissue, plant organ, plant or seed comprising
(a) introducing the expression cassette or the vector of the present invention into a plant cell; and
(b) regenerating said plant cell to form a plant tissue, plant organ, plant or seed.

In another aspect, the present invention refers to a method for producing a transgenic plant tissue, plant organ, plant or seed comprising
(a) integrating the expression cassette or the vector of the present invention into the genome of a plant cell;
(b) regenerating said plant cell to form a plant tissue, plant organ, plant or seed, and
(c) selecting said plant cell to form a plant tissue, plant organ, plant or seed for the presence of the expression cassette or the vector of the present invention.

Other embodiments of the invention relate to vectors comprising an expression cassette of the invention, and transgenic host cells or transgenic plant comprising an expression cassette or a vector of the invention, and methods of producing the same.

DESCRIPTION OF THE SEQUENCES

Figure 1:
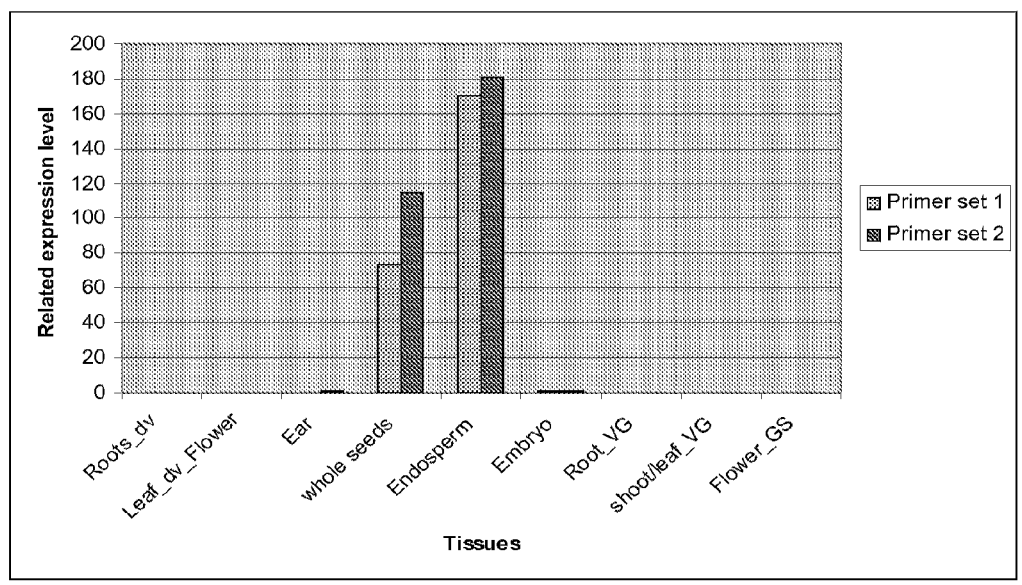
FIG. 1: q-RT-PCR results of MAWS21 showing whole seed and endosperm-specific expression

SEQ ID NO:1
p_MAWS21 promoter sequence (845 bp)
SEQ ID NO: 2
Coding sequence of MAWS21 gene
SEQ ID NO: 3
Deduced amino acid sequence of MAWS21 gene
SEQ ID NO: 4
Consensus sequence of ZM1s61995623 including 5'-UTR (bp 1-20), ORF, and 3'-UTR
SEQ ID NOs: 5-8
Primer sequences for q-RT-PCR
SEQ ID NOs: 9-10
GAPDH control primers forward and reverse for q-RT-PCR.
SEQ ID NO: 11-12
Primer sequences for p_MAWS21 cloning SEQ ID NO: 13
Maize genomic DNA sequence ZmGSStuc11-12-04.18117.1 including 5"-UTR (bp 847 to 866) of ZM1s61995623, CDS and 3'-UTR
SEQ ID NO: 14-24
Sequences of the selected cis-acting elements of p_MAWS21 having at least 10 nucleotides
SEQ ID NO: 25
Binary vector RTP1054
SEQ ID NO: 26
pMAWS21 promoter sequence
SEQ ID NO: 27:
pMAWS21_Variant2 (BVH replaced by BVH)
SEQ ID NO: 28
pMAWS21_Variant3 (BVH replaced by BVH plus stop codons)

GENERAL DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower).

As used herein, the word "or" means any one member of a particular list and also includes any combination of members of that list.

"Expression cassette" as used herein means a linear or circular nucleic acid molecule. It encompasses DNA as well as RNA sequences which are capable of directing expression of a particular nucleotide sequence in an appropriate host cell. In general, it comprises a promoter operably linked to a polynucleotide of interest, which is—optionally—operably linked to termination signals and/or other regulatory elements. The expression cassette of the present invention is characterized in that it shall comprise a transcription regulating nucleotide sequence as defined hereinafter. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the polynucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development (e.g., the seed-specific or seed-preferential promoters of the invention). In a preferred embodiment, such expression cassettes will comprise the transcriptional initiation region of the invention linked to a nucleotide sequence of interest. Such an expression cassette is preferably provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions and others described below (see also, Guerineau 1991; Proudfoot 1991; Sanfacon 1991; Mogen 1990; Munroe 1990; Ballas 1989; Joshi 1987). The expression cassette can also comprise a multiple cloning site. In such a case, the multiple cloning site is, preferably, arranged in a manner as to allow for operative linkage of a polynucleotide to be introduced in the multiple cloning site with the transcription regulating sequence. In addition to the aforementioned components, the expression cassette of the present invention, preferably, could comprise components required for homologous recombination, i.e. flanking genomic sequences from a target locus. However, also contemplated is an expression cassette which essentially consists of the transcription regulating nucleotide sequence, as defined hereinafter.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised, in some cases, of a TATA box and other sequences that serve to specify the site of transcription initiation, to which regulatory elements are added for enhancement of expression. "Promoter" also refers to a nucleotide sequence that includes a minimal promoter plus regulatory elements and that is capable of controlling the expression of a coding sequence or functional RNA. This type of promoter sequence consists of proximal and more distal upstream elements, the latter elements often referred to as enhancers. Accordingly, an "enhancer" is a DNA sequence, which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors, which control the effectiveness of transcription initiation in response to physiological or developmental conditions. The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative. Promoter elements, such as a TATA element, that are inactive or have greatly reduced promoter activity in the absence of upstream activation are referred as "minimal" or "core" promoters. In the presence of a suitable transcription factor, the minimal promoter functions to permit transcription. A "minimal" or "core" promoter thus consists only of all basal elements needed for transcription initiation, e.g., a TATA box and/or an initiator.

"Constitutive promoter" refers to a promoter that is able to express the open reading frame (ORF) in all or nearly all of the plant tissues during all or nearly all developmental stages of the plant. Each of the transcription-activating elements do not exhibit an absolute tissue-specificity, but mediate transcriptional activation in most plant tissues at a level of at least 1% reached in the plant tissue in which transcription is most active. "Constitutive expression" refers to expression using a constitutive promoter.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems. "Conditional" and "regulated expression" refer to expression controlled by a regulated promoter.

"Inducible promoter" refers to those regulated promoters that can be turned on in one or more cell types by an external stimulus, such as a chemical, light, hormone, stress, or a pathogen.

As used herein, "transcription regulating nucleotide sequence", refers to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating nucleotide sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed.

As used herein, the term "cis-regulatory element" or "promoter motif" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact in different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal of a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

The "expression pattern" of a promoter (with or without enhancer) is the pattern of expression levels, which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates. The rate of degradation can however be considered to proceed at a fixed rate when the transcribed sequences are identical, and thus this value can serve as a measure of synthesis rates. When promoters are compared in this way, techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA. The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription. A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression. Generally, individual transformed lines with one chimeric promoter reporter construct may vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence. For the purposes of the present invention, "tissue-specific" preferably refers to "seed-specific" or "seed-preferential".

"Seed" as used herein refers, preferably, to whole seed, endosperm and embryonic tissues, more preferably to endosperm. "Specific" in the sense of the invention means that the polynucleotide of interest being operatively linked to the transcription regulating nucleotide sequence referred to herein will be predominantly expressed in the indicated tissues or cells when present in a plant. A predominant expression as meant herein is characterized by a statistically significantly higher amount of detectable transcription in the said tissue or cells with respect to other plant tissues. A statistically significant higher amount of transcription is, preferably, an amount being at least two-fold, three-fold, four-fold, five-fold, ten-fold, hundred-fold, five hundred-fold or thousand-fold the amount found in at least one of the other tissues with detectable transcription. Alternatively, it is an expression in the indicated tissue or cell whereby the amount of transcription in other tissues or cells is less than 1%, 2%, 3%, 4% or, most preferably, 5% of the overall (whole plant) amount of expression. The amount of transcription directly correlates to the amount of transcripts (i.e. RNA) or polypeptides encoded by the transcripts present in a cell or tissue. Suitable techniques for measuring transcription either based on RNA or polypeptides are well known in the art. Tissue or cell specificity alternatively and, preferably in addition to the above, means that the expression is restricted or almost restricted to the indicated tissue or cells, i.e. there is essentially no detectable transcription in other tissues. Almost restricted as meant herein means that unspecific expression is detectable in less than ten, less than five, less than four, less than three, less than two or one other tissue(s). "Seed-preferential" in the context of this invention means the transcription of a nucleic acid sequence by a transcription regulating element in a way that transcription of said nucleic acid sequence in seeds contribute to more than 50%, preferably more than 70%, more preferably more than 80% of the entire quantity of the RNA transcribed from said nucleic acid sequence in the entire plant during any of its developmental stage.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

Seed specific expression can be determined by comparing the expression of a nucleic acid of interest, e.g., a reporter gene such as GUS, operatively linked to the expression control sequence in the following tissues and stages: 1) roots and leafs at 5-leaf stage, 2) stem at V-7 stage, 3) Leaves, husk, and silk at flowering stage at the first emergence of silk, 4) Spikelets/Tassel at pollination, 5) Ear or Kernels at 5, 10, 15, 20, and 25 days after pollination. Preferably, expression of the nucleic acid of interest can be determined only in Ear or Kernels at 5, 10, 15, 20, and 25 days after pollination in said assay as shown in the accompanying Figures. The expression of the polynucleotide of interest can be determined by various well known techniques, e.g., by Northern Blot or in situ hybridization techniques as described in WO 02/102970, and, preferably, by GUS histochemical analysis as described in the accompanying Examples. Transgenic plants for analyzing seed specific expression can be also generated by techniques well known to the person skilled in the art and as discussed elsewhere in this specification.

The term "nucleic acid" refers to deoxyribonucleotides or ribonucleotides and their polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals. The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence, i.e. for example to SEQ ID NO's:1, 2, 3, 4, 13.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. Nos. 5,605,794, 6, 8, 10, and 12,837,458).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra. Multiple alignments (i.e. of more than 2 sequences) are preferably performed using the Clustal W algorithm (Thompson 1994; e.g., in the software Vector NTI™, version 9; Invitrogen Inc.) with the scoring matrix BLOSUM62MT2 with the default settings (gap opening penalty $15/19$, gap extension penalty $6.66\%.05$; gap separation penalty range 8; % identity for alignment delay 40; using residue specific gaps and hydrophilic residue gaps).

Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy sonic positive-valued threshold score T when aligned with a word of the same length in a database sequence, T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See ncbi.nlm.nih.gov. Alignment may also be performed manually by inspection.

For purposes of the present invention, comparison of nucleotide sequences for determination of percent sequence identity to specific nucleotide sequences (e.g., the promoter sequences disclosed herein or the sequences encoding for the ZM1s61995623 protein and its orthologs) is preferably made using the BlastN program (version 1.4.7 or later) with its default parameters (wordlength (W) of 11, an expectation (E) of 10, a cutoff of 100, M=5, N=−4, and a comparison of both strands) or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

For purposes of the present invention, comparison of polypeptide or amino acid sequences for determination of percent sequence identity/homology to specific polypeptide or amino acid sequences (e.g., the sequences of the ZM1s61995623 protein) is preferably made using the BlastP program (version 1.4.7 or later) with its default parameters (wordlength (W) of 3, an expectation (E) of 10, and the BLOSUM62 scoring matrix (Henikoff & Henikoff, 1989); see ncbi.nlm.nih.gov) or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 38%, e.g., 39%, 40%, 42%, 44%, 46%, 48%, 50%, 52%, 54%, 56%, 58%, 60%, 62%, 64%, 65%, 66%, 67%, 68%, 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 38%, 50% or 60%, preferably at least 70% or 80%, more preferably at least 90%, 95%, and most preferably at least 98%. Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 38%, e.g. 39%, 40%, 42%, 44%, 46%, 48%, 50%, 52%, 54%, 56%, 58%, 60%, 62%, 64%, 65%, 66%, 67%, 68%, 69%, 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m = 81.5° C. + 16.6(\log_{10} M) + 0.41(\% GC) - 0.61(\% \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of highly stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C. (very low stringency conditions), more desirably in 7% sodium dodecyl sulfate (SDS), 0.5 M NaPO$_4$, 1 mM EDTA at 50° C. with washing in 1×SSC, 0.1% SDS at 50° C. (low stringency conditions), more desirably still in 7% sodium dodecyl sulfate (SDS), 0.5 M NaPO$_4$, 1 mM EDTA at 50° C. with washing in 0.5×SSC, 0.1% SDS at 50° C. (moderate stringency conditions), preferably in 7% sodium dodecyl sulfate (SDS), 0.5 M NaPO$_4$, 1 mM EDTA at 50° C. with washing in 0.1×SSC, 0.1% SDS at 50° C. (high stringency conditions), more preferably in 7% sodium dodecyl sulfate (SDS), 0.5 M NaPO$_4$, 1 mM EDTA at 50° C. with washing in 0.1× SSC, 0.1% SDS at 65° C. (very high stringency conditions).

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Encoding" or "Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequences of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

"Vector" is defined to include, inter alia, any plasmid, cosmid, phage or Agrobacterium binary nucleic acid molecule in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, kanamycin resistance, streptomycin resistance or ampicillin resistance.

A "transgene" or "transgenic" refers to a gene that has been introduced into the genome by transformation and is stably or transiently maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The term "transformation" refers to the transfer of a nucleic acid fragment into the genome of a host cell. Host cells containing the transformed nucleic acid fragments are referred to as "transgenic" cells, and organisms comprising transgenic cells are referred to as "transgenic organisms". Examples of methods of transformation of plants and plant cells include Agrobacterium-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999). For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as Agrobacterium-mediated transformation or biolistic bombardment), but not selected for stable maintenance.

"Stably transformed" refers to cells that have been selected and regenerated on a selection media following transformation.

"Chromosomally-integrated" refers to the integration of a foreign gene or DNA construct into the host genome by covalent bonds. Where genes are not "chromosomally integrated", they may be "transiently expressed". Transient expression of a gene refers to the expression of a gene that is not integrated into the host chromosome but functions independently, either as part of an autonomously replicating plasmid or expression cassette, for example, or as part of another biological system such as a virus. "Genetically stable" and "heritable" refer to chromosomally-integrated genetic elements that are stably maintained in the plant and stably inherited by progeny through successive generations.

A "transgenic plant" is a plant having one or more plant cells that contain an expression vector as defined hereinafter in the detailed description.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The term "altered plant trait" means any phenotypic or genotypic change in a transgenic plant relative to the wild-type or non-transgenic plant host.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom.

DETAILED DESCRIPTION OF THE INVENTION

The present invention thus provides isolated nucleic acid molecules comprising a plant nucleotide sequence that directs seed-preferential or seed-specific transcription of an operably linked nucleic acid fragment in a plant cell.

Specifically, the present invention provides an expression cassette for regulating seed-specific expression of a polynucleotide of interest, said expression cassette comprising a transcription regulating nucleotide sequence selected from the group of sequences consisting of:
(a) a nucleic acid sequence of SEQ ID NO: 1, or a variant thereof.
(b) a nucleic acid sequence which is at least 80% identical to a nucleic acid sequence shown in any one of SEQ ID NO: 1;
(c) a nucleic acid sequence which hybridizes under stringent conditions to a nucleic acid sequence of SEQ ID NO: 1;
(d) a nucleic acid sequence which hybridizes to a nucleic acid sequence located upstream of an open reading frame sequence of SEQ ID NO: 2;
(e) a nucleic acid sequence which hybridizes to a nucleic acid sequence located upstream of an open reading frame sequence encoding an amino acid sequence of SEQ ID NO: 3;
(f) a nucleic acid sequence which hybridizes to a nucleic acid sequence located upstream of an open reading frame sequence being at least 80% identical to an open reading frame sequence of SEQ ID NO: 2, wherein the open reading frame encodes a seed protein;
(g) a nucleic acid sequence which hybridizes to a nucleic acid sequences located upstream of an open reading frame encoding an amino acid sequence being at least 80% identical to an amino acid sequence as shown in SEQ ID NO: 3, wherein the open reading frame encodes a seed protein;
(h) a nucleic acid sequence obtainable by 5' genome walking or by thermal asymmetric interlaced polymerase chain reaction (TAIL-PCR) on genomic DNA from the first exon of an open reading frame sequence as shown in SEQ ID NO: 2; and
(i) a nucleic acid sequence obtainable by 5' genome walking or TAIL PCR on genomic DNA from the first exon of an open reading frame sequence being at least 80% identical to an open reading frame as shown in SEQ ID NO: 2, wherein the open reading frame encodes a seed protein; and
(j) a nucleic acid sequence obtainable by 5' genome walking or TAIL PCR on genomic DNA from the first exon of an open reading frame sequence encoding an amino acid sequence being at least 80% identical to an amino acid sequence encoded by an open reading frame as shown in SEQ ID NO: 3, wherein the open reading frame encodes a seed protein.

The ZM1s61995623 gene is encoding a putative uncharacterized protein (hereinafter also MAWS21). The seed-preferential or seed-specific promoters may be useful for expressing genes as well as for producing large quantities of protein, for expressing oils or proteins of interest, e.g., antibodies, genes for increasing the nutritional value of the seed and the like.

Preferably, the transcription regulating nucleotide sequence and promoters of the invention include a consecutive stretch of about 25 to 2000, including 50 to 500 or 100 to 250, and up to 1000 or 1500, contiguous nucleotides, e.g., 40 to about 845, 60 to about 845, 125 to about 845, 250 to about 845, 400 to about 845, 600 to about 845, upstream of the ATG that is located at position 867-869 of the ZmGSStuc11-12-04.18117.1, i.e. SEQ ID NO:13, which include the minimal promoter region. In a particular embodiment of the invention said consecutive stretch of about 25 to 2000, including 50 to 500 or 100 to 250, and up to 1000 or 1500, contiguous nucleotides, e.g., 40 to about 845, 60 to about 845, 125 to about 845, 250 to about 845, 400 to about 845, 600 to about 845, has at least 50% or 60%, preferably at least 70% or 80%, more preferably at least 90% and most preferably at least 95%, nucleic acid sequence identity with a corresponding consecutive stretch of about 25 to 2000, including 50 to 500 or 100 to 250, and up to 1000 or 1500, contiguous nucleotides, e.g., 40 to about 845, 60 to about 845, 125 to about 845, 250 to about 845, 400 to about 845, 600 to about 845, upstream of the ATG that is located at position 867-869 of SEQ ID NO: 13, which include the minimal promoter region. The above-defined stretch of contiguous nucleotides preferably comprises one or more promoter motifs, as shown in Table 5, preferably selected from the group consisting of TATA box, GC-box, CAAT-box and a transcription start site. A preferred transcription regulating nucleotide sequence to be included into an expression cassette of the present invention has a nucleic acid sequence as shown in SEQ ID NO: 1, or a variant thereof.

The present invention also contemplates a transcription regulating nucleotide sequences which can be derived from a transcription regulating nucleotide sequence shown in SEQ ID NO: 1. Said transcription regulating nucleotide sequences are capable of hybridizing, preferably under stringent conditions, to the upstream sequences of the open reading frame shown in SEQ ID NO. 2, or a variant thereof, i.e. to the transcription regulating nucleotide sequences shown in SEQ ID NO: 1, or a variant thereof.

Stringent hybridization conditions as meant herein are, preferably, hybridization conditions in 6× sodium chloride/sodium citrate (=SSC) at approximately 45° C., followed by one or more wash steps in 0.2×SSC, 0.1% SDS at 53 to 65° C., preferably at 55° C., 56° C., 57° C., 58° C., 59° C., 60° C., 61° C., 62° C., 63° C., 64° C. or 65° C. The skilled worker knows that these hybridization conditions differ depending on the type of nucleic acid and, for example when organic solvents are present, with regard to the temperature and concentration of the buffer. Examples for stringent hybridization conditions are given in the "General Definitions" section.

Moreover, transcription regulating nucleotide sequences of the present invention can not only be found upstream of the aforementioned open reading frames having a nucleic acid sequence as shown in SEQ ID NO. 2. Rather, transcription regulating nucleotide sequences can also be found upstream of orthologous, paralogous or homologous genes (i.e. open reading frames). Thus, also preferably, a variant transcription regulating nucleotide sequence comprised by an expression cassette of the present invention has a nucleic acid sequence which hybridizes to a nucleic acid sequences located upstream of an open reading frame sequence being at least 70%, more preferably, at least 80%, at least 90%, at least 91%, at least 92%, at least 93%, at least 94% at least 95%, at least 96%, at least 97%, at least 98%, or at least 99% identical to a sequence as shown in SEQ ID NO: 2. The said variant open reading shall encode a polypeptide having the biological activity of the corresponding polypeptide being encoded by the open reading frame shown in SEQ ID NO: 2. In this context it should be mentioned that the open reading frame shown in SEQ ID NO: 2 encodes a polypeptide having the amino acid sequence shown in SEQ ID NO: 3 and, preferably, encodes a seed protein.

Also preferably, a variant transcription regulating nucleotide sequence of the present invention is (i) obtainable by 5' genome walking or TAIL PCR from an open reading frame sequence as shown in SEQ ID NO: 2 or (ii) obtainable by 5' genome walking or TAIL PCR from a open reading frame sequence being at least 80% identical to an open reading frame as shown in SEQ ID NOs: 2. Variant expression control sequences are obtainable without further ado by the genome walking technology or by thermal asymmetric interlaced polymerase chain reaction (TAIL-PCR) which can be carried out as described in the accompanying Examples by using, e.g., commercially available kits.

Suitable oligonucleotides corresponding to a nucleotide sequence of the invention, e.g., for use as primers in probing or amplification reactions as the PCR reaction described above, may be about 30 or fewer nucleotides in length (e.g., 9, 12, 15, 18, 20, 21, 22, 23, or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

Particularly preferred primers for use in the present invention are shown in SEQ ID's:5, 6, 7, 8, and 11, and 12.

Variant transcription regulating nucleotide sequences referred to in this specification for the transcription regulating nucleotide sequence shown in SEQ ID NO: 1, preferably, comprise at least 10, at least 20, at least 30, or all of the sequence motifs recited in Table 5.

Examples for preferred variant transcription regulating sequences are shown in SEQ ID NOs: 27 and 28. Compared to the corresponding transcription regulating nucleotide sequences, the aforementioned variants (as shown in SEQ ID NOs: 27 and 28) do not comprise start codons (ATG). The start codons are either replaced by BVH or by BVH plus a stop codon between any two start codons (according to the IUPAC nomenclature: B represents C or G or T, V represents A or C or G, and H represents A or C or T). Thus, variant transcription regulating sequences may be obtained by mutating putative start codons as described above.

Without significantly impairing the properties mentioned, non-essential sequences of the transcription regulating nucleotide sequence of the invention can be deleted. Delimitation of the expression control sequence to particular essential regulatory regions can also be undertaken with the aid of a computer program such as the PLACE program ("Plant Cis-acting Regulatory DNA Elements") (Higo K et al. (1999) Nucleic Acids Res 27:1, 297-300), see Table 5, or the BIOBASE database "Transfac" (Biologische Datenbanken GmbH, Braunschweig). By such measures, variant transcription regulating nucleotide sequences as specified above can be artificially generated. Moreover, processes for mutagenizing nucleic acid sequences are known to the skilled worker and include, e.g., the use of oligonucleotides having one or more mutations compared with the region to be mutated (e.g. within the framework of a site-specific mutagenesis). Primers having approximately 15 to approximately 75 nucleotides or more are typically employed, with preferably about 10 to about 25 or more nucleotide residues being located on both sides of a sequence to be modified. Details and procedure for said mutagenesis processes are familiar to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be achieved by treatment of, for example, vectors comprising the transcription regulating nucleotide sequence of the invention with mutagenizing agents such as hydroxylamine. Mutagenesis also yields variant expression cassettes of the invention as specified above.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

Accordingly, a further embodiment of the present invention, the expression cassette of the present invention comprises at least one polynucleotide of interest being operatively linked to the transcription regulating nucleotide sequence and/or at least one a termination sequence or transcription. Thus, the expression cassette of the present invention, preferably, comprises a transcription regulating nucleotide sequence for the expression of at least one polynucleotide of interest. However, expression cassettes comprising transcription regulating nucleotide sequences with at least two, three, four or five or even more transcription regulating nucleotide sequences for polynucleotides of interest are also contemplated by the present invention.

The term "polynucleotide of interest" refers to a nucleic acid which shall be expressed under the control of the transcription regulating nucleotide sequence referred to herein. Preferably, a polynucleotide of interest encodes a polypeptide the presence of which is desired in a cell or plant seed as referred to herein. Such a polypeptide may be an enzyme which is required for the synthesis of seed storage compounds or may be a seed storage protein. It is to be understood that if the polynucleotide of interest encodes a polypeptide, transcription of the nucleic acid in RNA and translation of the transcribed RNA into the polypeptide may be required. A polynucleotide of interest, also preferably, includes biologically active RNA molecules and, more preferably, antisense RNAs, ribozymes, micro RNAs or siRNAs. For example, an undesired enzymatic activity in a seed can be reduced due to the seed specific expression of an antisense RNAs, ribozymes, micro RNAs or siRNAs. The underlying biological principles of action of the aforementioned biologically active RNA molecules are well known in the art. Moreover, the person skilled in the art is well aware of how to obtain nucleic acids which encode such biologically active RNA molecules. It is to be understood that the biologically active RNA molecules may be directly obtained by transcription of the nucleic acid of interest, i.e. without translation into a polypeptide. Preferably, at least one polynucleotide of interest to be expressed under the control of the transcription regulating nucleotide sequence of the present invention is heterologous in relation to said expression control sequence, i.e. it is not naturally under the control thereof, but said control has been produced in a non-natural manner (for example by genetic engineering processes)

An operable linkage may—for example—comprise an sequential arrangement of the transcription regulating nucleotide sequence of the invention (for example a sequence as described by SEQ ID NO: 1) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. The term "appropriate conditions" mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the polynucleotide of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NO: 1) into the plant genome. Such insertion will result in an operable linkage to a nucleic acid sequence of interest, which as such already existed in the genome. By the insertion the nucleic acid of interest is expressed in a seed-preferential or seed-specific way due to the transcription regulating properties of the transcription regulating nucleotide sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a polynucleotide of interest to be expressed may by inserted into a plant genome comprising the transcription regulating nucleotide sequence in its natural genomic environment (i.e. linked to its natural gene) in a way that the inserted sequence becomes operably linked to the transcription regulating nucleotide sequence, thereby forming an expression cassette of the invention.

The expression cassette may be employed for numerous expression purposes such as for example expression of a protein, or expression of a antisense RNA, sense or double-stranded RNA. Preferably, expression of the nucleic acid sequence confers to the plant an agronomically valuable trait.

The polynucleotide of interest to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant, which exhibits substantially no phenotypic changes as a consequence of agent administration, infection with a pathogen, or exposure to stress. By "tolerant" is meant a plant, which, although it may exhibit some phenotypic changes as a consequence of infection, does not have a substantially decreased reproductive capacity or substantially altered metabolism.

Seed-specific transcription regulating nucleotide sequences (e.g., promoters) are useful for expressing a wide variety of genes including those which alter metabolic pathways, confer disease resistance, for protein production, e.g., antibody production, or to improve nutrient uptake and the like. Seed-specific transcription regulating nucleotide sequences (e.g., promoters) may be modified so as to be regulatable, e.g., inducible. The genes and transcription regulating nucleotide sequences (e.g., promoters) described hereinabove can be used to identify orthologous genes and their transcription regulating nucleotide sequences (e.g., promoters) which are also likely expressed in a particular tissue and/or development manner. Moreover, the orthologous transcription regulating nucleotide sequences (e.g., promoters) are useful to express linked open reading frames. In addition, by aligning the transcription regulating nucleotide sequences (e.g., promoters) of these orthologs, novel cis elements can be identified that are useful to generate synthetic transcription regulating nucleotide sequences (e.g., promoters).

Another object of the present invention refers to a vector comprising the expression cassette of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment (e.g., "gene-gun"). Suitable methods for the transformation or transfection of host cells, including plant cells, can be found in Sambrook et al. (Molecular Cloning: A Laboratory Manual, 2$^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. An overview of binary vectors and their use can be found in Hellens et al, Trends in Plant Science (2000) 5, 446-451. Furthermore, by using appropriate cloning vectors, the expression cassette of the invention can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus, Annu. Rev. Plant Physiol. Plant Molec. Biol. 42 (1991), 205-225.

More preferably, the vector of the present invention is an expression vector. In such an expression vector, the expression cassette comprises a transcription regulating nucleotide sequence as specified above allowing for expression in eukaryotic cells or isolated fractions thereof. An expression vector may, in addition to the expression cassette of the invention, also comprise further regulatory elements including transcriptional as well as translational enhancers. Preferably, the expression vector is also a gene transfer or targeting vector. Expression vectors derived from viruses such as retroviruses, vaccinia virus, adeno-associated virus, herpes viruses, or bovine papilloma virus, may be used for delivery of the expression cassettes or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Suitable expression vector backbones are, preferably, derived from expression vectors known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the nucleic acid of interest encoding a protein to be expressed. The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. Examples of vectors for expression in the yeast *S. cerevisiae* comprise pYepSecI (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C.A.M.J.J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23.

The vector of the present invention comprising the expression cassette will have to be propagated and amplified in a suitable organism, i.e. expression host.

Accordingly, another embodiment of the invention relates to transgenic host cells or non-human, transgenic organisms comprising an expression cassette of the invention. Preferred are prokaryotic and eukaryotic organisms. Both microorganism and higher organisms are comprised. Preferred microorganisms are bacteria, yeast, algae, and fungi. Preferred bacteria are those of the genus *Escherichia, Erwinia, Agrobacterium, Flavobacterium, Alcaligenes, Pseudomonas, Bacillus* or *Cyanobacterim* such as—for example—*Synechocystis* and other bacteria described in Brock Biology of Microorganisms Eighth Edition (pages A-8, A-9, A10 and A11). Most preferably the transgenic cells or non-human, transgenic organisms comprising an expression cassette of the invention is a plant cell or plant (as defined above), more preferably a plant used for oil production such as—for example—*Brassica napus, Brassica juncea, Linum usitatissimum*, soybean, *Camelina* or sunflower.

Especially preferred are microorganisms capable to infect plants and to transfer DNA into their genome, especially bacteria of the genus *Agrobacterium*, preferably *Agrobacterium tumefaciens* and rhizogenes. Preferred yeasts are *Candida, Saccharomyces, Hansenula* and *Pichia*. Preferred fungi are *Aspergillus, Trichoderma, Ashbya, Neurospora, Fusarium*, and *Beauveria*.

In a preferred embodiment of the present invention, the host cell relates to a plant cell, plant, a plant seed, a non-human animal or a multicellular micro-organism.

Accordingly, the present invention further refers to a transgenic plant cell, plant tissue, plant organ, or plant seed, comprising the expression cassette or the vector of the present invention.

The expression cassette or vector may be present in the cytoplasm of the organism or may be incorporated into the genome either heterologous or by homologous recombination. Host cells, in particular those obtained from plants or animals, may be introduced into a developing embryo in order to obtain mosaic or chimeric organisms, i.e. transgenic organisms, i.e. plants, comprising the host cells of the present invention. Suitable transgenic organisms are, preferably, all organisms which are suitable for the expression of recombinant genes.

The nature of the transgenic plant cells is not limited, for example, the plant cell can be a monocotyledonous plant cell, or a dicotyledonous plant cell. Preferably, the transgenic plant transgenic plant tissue, plant organ, plant or seed is a monocotyledonous plant or a plant cell, plant tissue, plant organ, plant seed from a monocotyledonous plant.

Examples of transgenic plant cells finding use with the invention include cells (or entire plants or plant parts) derived from the genera: *Ananas, Musa, Vitis, Fragaria, Lotus, Medicago, Onobrychis, Trifolium, Trigonella, Vigna, Citrus, Carica, Persea, Prunus, Syragrus, Theobroma, Coffea, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Mangifera, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucurbita, Cucumis, Browaalia, Lolium, Malus, Apium, Gossypium, Vicia, Lathyrus, Lupinus, Pachyrhizus, Wisteria, Stizolobium, Agrostis, Phleum, Dactylis, Sorghum, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Psidium, Passiflora, Cicer, Phaseolus, Lens*, and *Arachis*

Preferably, the transgenic plant cells finding use with the invention include cells (or entire plants or plant parts) from the family of poaceae, such as the genera *Hordeum, Secale, Avena, Sorghum, Andropogon, Holcus, Panicum, Oryza, Zea, Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum, Secale cereale, Avena sativa, Avena fatua, Avena byzantina, Avena fatua* var. *sativa, Avena hybrida, Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum, Oryza sativa, Oryza latifolia, Zea mays, Triticum aestivum, Triticum durum, Triticum turgidum, Triticum hybernum, Triticum macha, Triticum sativum* or *Triticum vulgare*.

In particular, preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, macadamia, avocado, bay, pumpkin/squash, linseed, soybean, pistachios, borage, trees (oil palm, coconut, walnut) or crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula*,

*Punica*, evening primrose, pumpkin/squash, linseed, soybean, borage, trees (oil palm, coconut).

In another aspect, the present invention relates to a method for producing a transgenic plant tissue, plant organ, plant or seed comprising
(a) introducing the expression cassette of any one of claims 1 to 3 or the vector of claim 4 or 5 into a plant cell; and
(b) regenerating said plant cell to form a plant tissue, plant organ, plant or seed.

Expression cassettes can be introduced into plant cells in a number of art-recognized ways. Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545, 818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid-targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known.

Various *Agrobacterium* strains can be employed, preferably disarmed *Agrobacterium tumefaciens* or rhizogenes strains. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101[pEHA101] (Hood 1986), EHA105 [pEHA105] (Li 1992), LBA4404[pAL4404](Hoekema 1983), C58C1[pMP90] (Koncz & Schell 1986), and C58C1 [pGV2260] (Deblaere 1985). Other suitable strains are *Agrobacterium tumefaciens* C58, a nopaline strain.

Other suitable strains are *A. tumefaciens* C58C1 (Van Larebeke 1974), A136 (Watson 1975) or LBA4011 (Klapwijk 1980). In another preferred embodiment the soil-borne bacterium is a disarmed variant of *Agrobacterium rhizogenes* strain K599 (NCPPB 2659). Preferably, these strains are comprising disarmed plasmid variants of a Ti- or Ri-plasmid providing the functions required for T-DNA transfer into plant cells (e.g., the vir genes). In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of *Agrobacterium tumefaciens* strain LBA4404 (Hiei 1994) with super-virulent plasmids. These are preferably pTOK246-based vectors (Ishida 1996).

A binary vector or any other vector can be modified by common DNA recombination techniques, multiplied in *E. coli*, and introduced into *Agrobacterium* by e.g., electroporation or other transformation techniques (Mozo & Hooykaas 1991).

*Agrobacterium* is grown and used in a manner similar to that described in Ishida (1996). The vector comprising *Agrobacterium* strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C.

The transformation of the target tissue (e.g., an immature embryo) by the *Agrobacterium* may be carried out by merely contacting the target tissue with the *Agrobacterium*. The concentration of *Agrobacterium* used for infection and co-cultivation may need to be varied. For example, a cell suspension of the *Agrobacterium* having a population density of approximately from $10^5$-$10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the *Agrobacterium*.

Preferably, the bacterium is employed in concentration of $10^6$ to $10^{10}$ cfu/ml. In a preferred embodiment for the co-cultivation step about 1 to 10 μl of a suspension of the soil-borne bacterium (e.g., *Agrobacteria*) in the co-cultivation medium are directly applied to each target tissue explant and air-dried. This is saving labor and time and is reducing unintended *Agrobacterium*-mediated damage by excess *Agrobacterium* usage.

For *Agrobacterium* treatment, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defence responses (like phenolic oxidation) may further improve the efficiency of *Agrobacterium*-mediated transformation. In another preferred embodiment, the co-cultivation medium of comprises least one thiol compound, preferably selected from the group consisting of sodium thiolsulfate, dithiothreitol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 μM to about 10 μM of silver nitrate and from about 50 mg/L to about 1,000 mg/L of L-Cystein. This results in a highly reduced vulnerability of the target tissue against *Agrobacterium*-mediated damage (such as induced necrosis) and highly improves overall transformation efficiency.

Various vector systems can be used in combination with *Agrobacteria*. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

In a preferred embodiment, the vector comprises a nucleic acid having the SEQ ID NO: 25.

Methods using either a form of direct gene transfer or *Agrobacterium*-mediated transfer usually, but not necessarily, are undertaken with a selectable marker, which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

Methods for the production and further characterization of stably transformed plants are well-known to the person skilled in the art. As an example, transgenic plant cells are placed in an appropriate selective medium for selection of transgenic cells, which are then grown to callus. Shoots are grown from callus. Plantlets are generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA, which has been introduced. Components of DNA constructs including transcription cassettes of this invention may be prepared from sequences, which are native (endogenous) or foreign (exogenous) to the host. By "foreign" it is meant that the sequence is not found in the wild-type host into which the construct is introduced. Heterologous constructs will contain at least one region, which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR or TaqMan; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using these technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Known methods of PCR include, but are not limited to, methods using paired primers, nested primers, single specific primers, degenerate primers, gene-specific primers, vector-specific primers, partially mismatched primers, and the like.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

The following section provides examples of particular polynucleotides of interest, which can be operably linked to the expression cassette of the present invention.

1. Exemplary Transgenes 1.1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

1.2 Insect Resistance

An important aspect of the present invention concerns the introduction of insect resistance-conferring genes into plants. Potential insect resistance genes, which can be introduced, include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA (c) genes. Endotoxin genes from other species of *B. thuringiensis*, which affect insect growth or development, may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes, which encode inhibitors of the insects' digestive system, or those that encode enzymes or cofactors that facilitate the production of inhibitors, may also be useful. Cystatin and amylase inhibitors, such as those from wheat and barley, may exemplify this group.

Also, genes encoding lectins may confer additional or alternative insecticide properties. Lectins (originally termed phytohemagglutinins) are multivalent carbohydrate-binding proteins, which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes, which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn rootworm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987), which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loom is 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes, which are not sugars, include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression or tissue-specific of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences, which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic cryIA(b) and cryIA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164). Other nucleic acid sequences which may be advantageously used herein include traits for insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), and bacterial disease resistance (U.S. Pat. No. 5,516,671).

1.5 Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene, which encodes an enzyme capable of rendering the mycotoxin nontoxic, would be useful in order to achieve reduced mycotoxin contamination of grain. The result of any of the above mechanisms would be a reduced presence of mycotoxins on grain.

1.6 Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway that are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring 1991). Additionally, the introduced DNA may encode enzymes, which degrade zeines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other well-known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below. Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA, which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase, which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups, which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping, quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

1.7 Tuber or Seed Composition or Quality

Various traits can be advantageously expressed especially in seeds or tubers to improve composition or quality. Useful nucleic acid sequences that can be combined with the promoter nucleic acid sequence of the present invention and provide improved end-product traits include, without limitation, those encoding seed storage proteins, fatty acid pathway enzymes, tocopherol biosynthetic enzymes, amino acid biosynthetic enzymes, and starch branching enzymes. A discussion of exemplary heterologous DNAs useful for the modification of plant phenotypes may be found in, for example, U.S. Pat. Nos. 6,194,636; 6,207,879; 6,232,526; 6,426,446; 6,429,357; 6,433,252; 6,437,217; 6,515,201; and 6,583,338 and PCT Publication WO 02/057471, each of which is specifically incorporated herein by reference in its entirety. Such traits include but are not limited to:

Expression of metabolic enzymes for use in the food-and-feed sector, for example of phytases and cellulases. Especially preferred are nucleic acids such as the artificial cDNA, which encodes a microbial phytase (GenBank Acc. No.: A19451) or functional equivalents thereof.

Expression of genes, which bring about an accumulation of fine chemicals such as of tocopherols, tocotrienols or carotenoids. An example, which may be mentioned is phytoene desaturase. Preferred are nucleic acids, which encode the Narcissus pseudonarcissus photoene desaturase (GenBank Acc. No.: X78815) or functional equivalents thereof. Preferred tocopherol biosynthetic enzymes include tyrA, slr1736, ATPT2, dxs, dxr, GGPPS, HPPD, GMT, MT1, tMT2, AANT1, slr 1737, and an antisense construct for homogentisic acid dioxygenase (Kridl et al., Seed Sci. Res., 1:209:219 (1991); Keegstra, Cell, 56(2):247-53 (1989); Nawrath et al., Proc. Natl. Acad. Sci. USA, 91:12760-12764 (1994); Xia et al., J. Gen. Microbiol., 138:1309-1316 (1992); Lois et al., Proc. Natl. Acad. Sci. USA, 95 (5):2105-2110 (1998); Takahashi et al., Proc. Natl. Acad. Sci. USA, 95(17):9879-9884 (1998); Norris et al., Plant Physiol., 117:1317-1323 (1998); Bartley and Scolnik, Plant Physiol., 104:1469-1470 (1994); Smith et al., Plant J., 11:83-92 (1997); WO 00/32757; WO 00/10380; Saint Guily et al., Plant Physiol., 100(2):1069-1071 (1992); Sato et al., J. DNA Res., 7(1):31-63 (2000)) all of which are incorporated herein by reference.

starch production (U.S. Pat. Nos. 5,750,876 and 6,476,295), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648), low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference. Preferred starch branching enzymes (for modification of starch properties) include those set forth in U.S. Pat. Nos. 6,232,122 and 6,147,279; and PCT Publication WO 97/22703, all of which are incorporated herein by reference.

Modified oils production (U.S. Pat. No. 6,444,876), high oil production (U.S. Pat. Nos. 5,608,149 and 6,476,295), or modified fatty acid content (U.S. Pat. No. 6,537,750). Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), diacylglycerol acyltransferases (U.S. Patent Publications 20030115632A1, 2, 3, 4, 5, 6, 7, 8, and 90030028923A1), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249) all of which are incorporated herein by reference.

Preferred amino acid biosynthetic enzymes include anthranilate synthase (U.S. Pat. No. 5,965,727 and PCT Publications WO 97/26366, WO 99/11800, WO 99/49058), tryptophan decarboxylase (PCT Publication WO 99/06581), threonine decarboxylase (U.S. Pat. Nos. 5,534,421 and 5,942,660; PCT Publication WO 95/19442), threonine deaminase (PCT Publications WO 99/02656 and WO 98/55601), dihydrodipicolinic acid synthase (U.S. Pat. No. 5,258,300), and aspartate kinase (U.S. Pat. Nos. 5,367,110; 5,858,749; and 6,040,160) all of which are incorporated herein by reference.

Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the *Bertholletia excelsa* high-methionine 2S albumin (GenBank Acc. No.: AB044391), the *Physcomitrella patens* 6-acyl-lipid desaturase (GenBank Acc. No.: AJ222980; Girke et al. (1998) Plant J 15:39-48), the *Mortierella alpina* 6-desaturase (Sakuradani et al. 1999 Gene 238:445-453), the *Caenorhabditis elegans* 5-desaturase (Michaelson et al. 1998, FEBS Letters 439:215-218), the *Caenorhabditis elegans* 5-fatty acid desaturase (des-5) (GenBank Acc. No.: AF078796), the *Mortierella alpina* 5-desaturase (Michaelson et al. JBC 273:19055-19059), the *Caenorhabditis elegans* 6-elongase (Beaudoin et al. 2000, PNAS 97:6421-6426), the *Physcomitrella patens* 6-elongase (Zank et al. 2000, Biochemical Society Transactions 28:654-657), or functional equivalents of these.

Production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described by Hood E E, Jilka J M (1999) Curr Opin Biotechnol 10(4): 382-6; Ma J K, Vine N D (1999) Curr Top Microbiol Immunol 236:275-92). For example, it has been possible to produce recombinant avidin from chicken albumen and bacterial -glucuronidase (GUS) on a large scale in transgenic maize plants (Hood et al. (1999) Adv Exp Med Biol 464:127-47. Review).

Obtaining an increased storability in cells which normally comprise fewer storage proteins or storage lipids, with the purpose of increasing the yield of these substances, for example by expression of acetyl-CoA carboxylase. Preferred nucleic acids are those, which encode the *Medicago sativa* acetyl-CoA carboxylase (ACCase) (GenBank Acc. No.: L25042), or functional equivalents thereof. Alternatively, in some scenarios an increased storage protein content might be advantageous for high-protein product production. Preferred seed storage proteins include zeins (U.S. Pat. Nos. 4,886,878; 4,885,357; 5,215,912; 5,589,616; 5,508,468; 5,939,599; 5,633,436; and 5,990,384; PCT Publications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (PCT Publication WO 96/17064), albumin (PCT Publication WO 97/35023), b-conglycinin (PCT Publication WO 00/19839), 11S (U.S. Pat. No. 6,107,051), alpha-hordothionin (U.S. Pat. Nos. 5,885,802 and 5,88,5801), arcelin seed storage proteins (U.S. Pat. No. 5,270,200), lectins (U.S. Pat. No. 6,110,891), and glutenin (U.S. Pat. Nos. 5,990,389 and 5,914,450) all of which are incorporated herein by reference.

Reducing levels of -glucan L-type tuber phosphorylase (GLTP) or -glucan H-type tuber phosphorylase (GHTP) enzyme activity preferably within the potato tuber (see U.S. Pat. No. 5,998,701). The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Reduction of GLTP or GHTP activity within the potato tuber may be accomplished by such techniques as suppression of gene expression using homologous antisense or double-stranded RNA, the use of co-suppression, regulatory silencing sequences. A potato plant having improved cold-storage characteristics, comprising a potato plant transformed with an expression cassette having a TPT promoter sequence operably linked to a DNA sequence comprising at least 20 nucleotides of a gene encoding an -glucan phosphorylase selected from the group consisting of glucan L-type tuber phosphorylase (GLTP) and glucan H-type phosphorylase (GHTP).

Further examples of advantageous genes are mentioned for example in Dunwell J M, Transgenic approaches to crop improvement, J Exp Bot. 2000; 51 Spec No; pages 487-96.

1.8 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plants of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes, which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilates into the grain and thus increase yield. Overexpression of genes within plants that are associated with "stay green" or the expression of any gene that delays senescence would be advantageous. For example, a non-yellowing mutant has been identified in *Festuca* pratensis (Davies 1990). Expression of this gene as well as others may prevent premature breakdown of chlorophyll and thus maintain canopy function.

1.9 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.10 Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani 1990). For example, a number of mutations were discovered in maize that confer cytoplasmic male sterility. One mutation in particular, referred to as T cytoplasm, also correlates with sensitivity to Southern corn leaf blight. A DNA sequence, designated TURF-13 (Levings 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

1.11. Non-Protein-Expressing Sequences 1.11.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsRNAi) is well known in the art and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants, which possess them. The transgenic plants may possess reduced levels of polypeptides including but not limited to the polypeptides cited above that may be affected by antisense RNA.

It is also possible that genes may be introduced to produce novel transgenic plants, which have reduced expression of a native gene product, by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.11.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element, which may be introduced, is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., seed-, root, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers, which encode a secretable antigen that can be identified by antibody interaction, or even secretable enzymes, which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for plant transformation. Such markers may include but are not limited to:

2.1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide), which suppresses growth of an untransformed wild type tissue. Especially preferred negative selection markers are those, which confer resistance to herbicides. Examples, which may be mentioned, are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.

altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A1 0 218 571).

Glyphosate® degrading enzymes (Glyphosate® oxidoreductase; gox),

Dalapon® inactivating dehalogenases (deh)

sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)

Bromoxynil® degrading nitrilases (bxn; Stalker 1988)

Kanamycin- or geneticin (G418) resistance genes (NPTII; NPT or neo; Potrykus 1985) coding e.g., for neomycin phosphotransferases (Fraley 1983; Nehra 1994)

2-Desoxyglucose-6-phosphate phosphatase ($DOG^R1$-Gene product; WO 98/45456; EP 0 807 836) conferring resistance against 2-desoxyglucose (Randez-Gil 1995).

hygromycin phosphotransferase (HPT), which mediates resistance to hygromycin (Vanden Elzen 1985).

altered dihydrofolate reductase (Eichholtz 1987) conferring resistance against methotrexat (Thillet 1988);

mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/l may be included in the medium. For example, with the daol gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 3 to 100 mg/l may be included in the medium. Typical concentrations for selection are 20 to 40 mg/l.

2.1.2 Positive Selection Marker Furthermore, positive selection marker can be employed. Genes like isopentenyltransferase from *Agrobacterium tumefaciens* (strain: PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) -Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), tms2 gene products (Fedoroff & Smith 1993), or -naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an -amylase gene (Ikuta 1990); a tyrosinase gene (Katz 1983) which encodes an enzyme capable of oxidizing tyrosine to DOPA and dopaquinone which in turn condenses to form the easily detectable compound melanin; -galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is dominant for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant, which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutraceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding, which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross-pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, which for example increase the effectiveness of conventional methods such as herbicide or pesticide treatment or allow dispensing with said methods due to their modified genetic properties. Alternatively new crops with improved stress tolerance can be obtained which, due to their optimized genetic "equipment", yield harvested product of better quality than products, which were not able to tolerate comparable adverse developmental conditions.

EXAMPLES

Materials and General Methods

Unless indicated otherwise, chemicals and reagents in the Examples were obtained from Sigma Chemical Company (St.

Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Identification of Transcript of MAWS21

A microarray study was conducted to identify transcripts with whole seed-specific expression in maize using the same panel of maize RNA samples shown in Table 1. The twenty-three labeled RNAs of these maize tissues were hybridized separately to 23 of our custom designed BPS maize Affymetrix chips, labeled with fluorescent streptavidin antibody, washed, stained and scanned as instructed in the Affymetrix Expression Analysis Technical Manual.

The chip hybridization data were analyzed using Genedata Specialist software and relative expression level was determined based on the hybridization signal intensity of each tissue.

TABLE 1

Corn Tissues used for mRNA expression profiling experiment

| Sample No. | Tissue | Timing and number of plants | Days after Pollination |
|---|---|---|---|
| 1 | Root | 9 am (4 plants) | 5 |
| 2 | | 9 am (4 plants) | 15 |
| 3 | | 9 am (4 plants) | 30 |
| 4 | leaf above the ear | 9 am (6 plants) | 5 |
| 5 | | 9 am (6 plants) | 15 |
| 6 | | 9 am (6 plants) | 30 |
| 7 | ear complete | 9 am (6 plants) | 5 |
| 8 | | 9 am (6 plants) | 10 |
| 9 | Whole seed | 9 am (6 plants) | 15 |
| 10 | | 9 am (6 plants) | 20 |
| 11 | | 9 am (6 plants) | 30 |
| 12 | Endosperm | 9 am (6 plants) | 15 |
| 13 | | 9 am (6 plants) | 20 |
| 14 | | 9 am (6 plants) | 30 |
| 15 | Embryo | 9 am (6 plants) | 15 |
| 16 | | 9 am (6 plants) | 20 |
| 17 | | 9 am (6 plants) | 30 |
| 18 | Female pistilate flower | 6 plants | before pollination |
| 19 | germinating seed | 20 seeds | imbibition for 3 days |
| 20 | root, veg. state | | V2 |
| 21 | root, veg. state | | V4 |
| 22 | leaf, veg. State | | V2 |
| 23 | leaf, veg. State | | V4 |

One BPS maize chip probe set, ZM1s61995623, was selected as candidate transcripts showing specifically expression in whole seeds and in endosperm as compared to other tissues.

Example 2

Confirmation of Expression Pattern of MAWS21 Using Quantitative Reverse Transcriptase-Polymerase Chain Reaction (q-RT-PCR)

Confirmation of the native expression pattern of MAWS21 was carried out via quantitative reverse transcription PCR (q-RT-PCR) using total RNA isolated from the same materials as were used for the chip hybridization study (Table 1).

Primers for qRT-PCR were designed based on the sequences of ZM1s61995623 using Vector NTI software package. Two sets of primers were used for PCR amplification. The sequences of primers are in Table 2. The glyceraldehyde-3-phosphate dehydrogenase (GAPDH) gene served as a control for normalization.

TABLE 2

Primer sequences for q-RT-PCR

Figure 2:
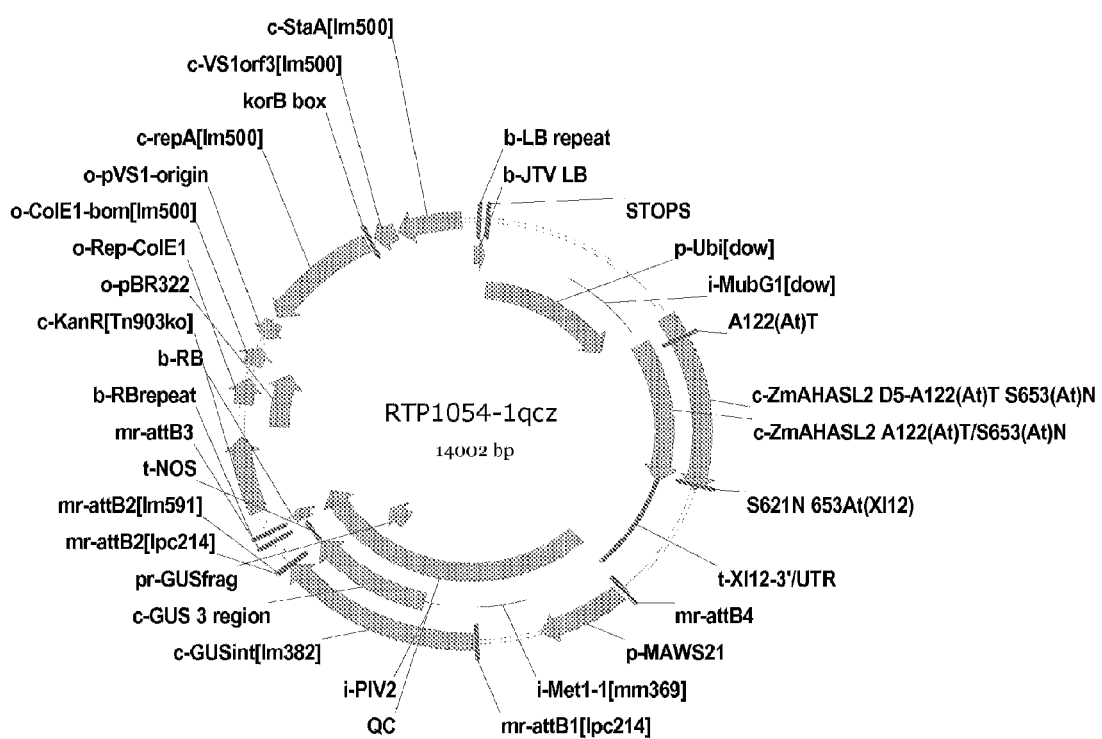
FIG. 2: Diagram of the vector RTP1054

| Primer | Sequence | SEQ ID NO: |
|---|---|---|
| MAWS21_forward1 | GGCCATGTCGGCGCAGTTCACA | 5 |
| MAWS21_reverse1 | CAGGGCCACGGCCGTCAAATAC | 6 |
| MAWS21_forward2 | GTGTGGGGTGGAGAGGGAGGGTC | 7 |
| MAWS21_reverse2 | CGCGTCTGACCACCTGTGTCGGTA | 8 |
| GAPDH_forward | GTAAAGTTCTTCCTGATCTGAAT | 9 |
| GAPDH_reverse | TCGGAAGCAGCCTTAATA | 10 | q-RT-PCR was performed using SuperScript III Reverse Transcriptase (Invitrogen, Carlsbad, Calif., USA) and SYBR Green QPCR Master Mix (Eurogentec, San Diego, Calif., USA) in an ABI Prism 7000 sequence detection system. cDNA was synthesized using 2-3 g of total RNA and 1 µL reverse transcriptase in a 20 L volume. The cDNA was diluted to a range of concentrations (15-20 ng/L). Thirty to forty ng of cDNA was used for quantitative PCR (qPCR) in a 30 L volume with SYBR Green QPCR Master Mix following the manufacturer's instruction. The thermocycling conditions were as follows: incubate at 50° C. for 2 minutes, denature at 95° C. for 10 minutes, and run 40 cycles at 95° C. for 15 seconds and 60° C. for 1 minute for amplification. After the final cycle of the amplification, the dissociation curve analysis was carried out to verify that the amplification occurred specifically and no primer dimer product was generated during the amplification process. The housekeeping gene glyceraldehyde-3-phosphate-dehydrogenase (GAPDH, primer sequences in Table 2) was used as an endogenous reference gene to normalize the calculation using the Comparative Ct (Cycle of threshold) value method. The $\Delta C_T$ value was obtained by subtracting the Ct value of GAPDH gene from the Ct value of the candidate genes. The relative transcription quantity (expression level) of the MAWS21 gene expression was presented as $2^{\Delta C_T}$. The qRT-PCR results were summarized in FIG. 2. Both primer sets gave same expression patterns as were obtained in the microarray study. which was specifically expression in whole seed and in endosperm.

Example 3

Annotation of MAWS21

The coding sequence corresponding to the MAWS21 gene was annotated based on in silico results obtained from both BLASTX of the chip probe consensus sequences of ZM1s61995623 against GenBank protein database (nr) and results from the translation program of Vector NTI software package. The ZM1s61995623 encodes a protein that homologs to a maize unknown protein (GenBank Accession: ACF78165.1). The top 10 homologous sequences from the BLASTX query are presented in Table 3.

TABLE 3

BLASTX search results of the maize ZM1s61995623 (MAWS21)

| Accession | Description | Score | E-value | % Identities |
|---|---|---|---|---|
| ACF78165.1 | unknown [*Zea mays*] | 215 | e−121 | 63 |
| ACF86030.1 | unknown [*Zea mays*] | 194 | e−111 | 58 |
| ACF83516.1 | unknown [*Zea mays*] | 140 | e−106 | 60 |
| ACF78865.1 | unknown [*Zea mays*] | 110 | 8.00E−70 | 80 |
| ACF87441.1 | unknown [*Zea mays*] | 183 | 1.00E−49 | 57 |
| ABI24164.1 | beta-glucosidase aggregating factor [*Sorghum bicolor*] | 122 | 4.00E−42 | 45 |
| EAY82651.1 | hypothetical protein OsI_036610 [*Oryza sativa* (*indica* cultivar-group)] | 73 | 4.00E−40 | 48 |
| NP_001066495.1 | Os12g0247700 [*Oryza sativa* (*japonica* cultivar-group)] | 68 | 3.00E−39 | 44 |
| NP_001066367.1 | Os12g0198700 [*Oryza sativa* (*japonica* cultivar-group)] | 63 | 1.00E−38 | 42 |
| AAR20919.1 | jasmonate-induced protein [*Triticum aestivum*] | 57 | 5.00E−36 | 55 |

Example 4

Identification of the Promoter Region of MAWS21

For our promoter identification purposes, the sequence upstream of the start codon of the MAWS21 gene was defined as the promoter p-MAWS21. To identify this predicted promoter region, the sequence of ZM1s61995623 was mapped to the BASF Plant Science proprietary maize genomic DNA sequence database, PUB_zmdb_genomesurveyseqs.nt. One maize genomic DNA sequences, ZmGSStuc11-12-04.18117.1 (2192 bp) was identified (SEQ ID NO: 13). This 2192 bp sequence harbored the predicted CDS of the corresponding gene to MAWS21 and about 800 bp upstream sequence of the ATG start codon of this gene.

Example 5

Isolation of the Promoter Region by PCR Amplification

The putative promoter region was isolated via genomic PCR using the following sequence specific primers:

Forward primer: TTTACTAAATCACGATAAATAAAA (SEQ ID NO: 11)

Reverse primer: GAGGGTTCTCCATTGGCCTG (SEQ ID NO: 12). The expected 845 bp fragment was amplified from maize genomic DNA, and named as promoter MAWS21 (p-MAWS21).

Example 6

BLASTN Results of p_MAWS21

The top 18 homologous sequences identified in the BlastN query of p_MAWS21 are presented in Table 4.

TABLE 4

BLASTN results of p_MAWS21

| Accession | Description | Max score | Total score | Query coverage | E value | Max ident |
|---|---|---|---|---|---|---|
| AC144700.2 | *Oryza sativa* (japonica cultivar-group) chromosome 11 BAC clone OSJN-Ba0017H17, complete sequence | 53.6 | 53.6 | 7% | 0.002 | 80% |
| AC114828.2 | *Oryza sativa* (japonica cultivar-group) chromosome 11 clone OSJNBb0038L23, complete sequence | 53.6 | 94.5 | 7% | 0.002 | 80% |
| AP008217.1 | *Oryza sativa* (japonica cultivar-group) genomic DNA, chromosome 11 | 53.6 | 94.5 | 7% | 0.002 | 80% |

TABLE 4-continued

| | BLASTN results of p_MAWS21 | | | | | |
|---|---|---|---|---|---|---|
| Accession | Description | Max score | Total score | Query coverage | E value | Max ident |
| EU952914.1 | *Zea mays* clone 1357151 unknown mRNA | 50 | 50 | 4% | 0.018 | 87% |
| BT036130.1 | *Zea mays* full-length cDNA clone ZM_BFb0097H02 mRNA, complete cds | 50 | 50 | 4% | 0.018 | 89% |
| NM_001137898.1 | *Zea mays* hypothetical protein LOC100192695 (LOC100192695), mRNA >gb\|BT034750.1\| *Zea mays* full-length cDNA clone ZM_BFb0015G01 mRNA, complete cds | 50 | 50 | 4% | 0.018 | 89% |
| BT042256.1 | *Zea mays* full-length cDNA clone ZM_BFb0181G14 mRNA, complete cds | 48.2 | 48.2 | 4% | 0.064 | 85% |
| BT018393.1 | *Zea mays* clone EL01N0319H05.d mRNA sequence | 48.2 | 48.2 | 5% | 0.064 | 82% |
| BT039113.1 | *Zea mays* full-length cDNA clone ZM_BFb0371D07 mRNA, complete cds | 46.4 | 46.4 | 3% | 0.22 | 93% |
| NM_001138024.1 | *Zea mays* hypothetical protein LOC100192833 (LOC100192833), mRNA >gb\|BT034926.1\| *Zea mays* full-length cDNA clone ZM_BFb0028J24 mRNA, complete cds | 46.4 | 46.4 | 4% | 0.22 | 85% |
| CP000383.1 | *Cytophaga hutchinsonii* ATCC 33406, complete genome | 46.4 | 46.4 | 4% | 0.22 | 88% |
| AB180901.1 | *Brassica oleracea* S-12 SRK gene for S-locus receptor kinase, complete cds | 46.4 | 46.4 | 4% | 0.22 | 88% |
| AF320614.3 | *Zea mays* anthocyanin regulatory C1 (c1) gene, C1-1170 allele, complete cds | 46.4 | 46.4 | 4% | 0.22 | 87% |
| AP008213.1 | *Oryza sativa* (japonica cultivar-group) genomic DNA, chromosome 7 | 46.4 | 46.4 | 6% | 0.22 | 81% |
| AP004670.4 | *Oryza sativa* Japonica Group genomic DNA, chromosome 7, PAC clone: P0496D04 | 46.4 | 46.4 | 6% | 0.22 | 81% |
| AP003843.3 | *Oryza sativa* Japonica Group genomic DNA, chromosome 7, BAC clone: OJ1656_E11 | 46.4 | 46.4 | 6% | 0.22 | 81% |
| EU970355.1 | *Zea mays* clone 343664 unknown mRNA | 44.6 | 44.6 | 5% | 0.78 | 82% |
| EU961051.1 | *Zea mays* clone 230717 unknown mRNA | 44.6 | 44.6 | 4% | 0.78 | 83% |

Example 7

PLACE Analysis of the Promoter MAWS21

Cis-acting motifs in the 845 bp of p-MAWS21 promoter region were identified using PLACE (a database of Plant Cis-acting Regulatory DNA elements) using the Genomatix database suite. The results are listed in Table 5. Four TATA box motifs were found in this promoter, located at nucleotide position 358-364, 371-377, 787-796 and 788-794 of the forward strand, respectively. Two CAAT box motifs were found at the nucleotide position 798-802 and 830-834 of the forward strand.

TABLE 5

PLACE analysis results of the 845 bp promoter p-MAWS21

| IUPAC Family IUPAC | Start pos. | End pos. | Strand | Mismatches | Score | Sequence | SEQ ID NO: |
|---|---|---|---|---|---|---|---|
| FAM012 IBOXCORE | 14 | 20 | + | 0 | 1 | GATAAAT | |
| FAM002 SORLIP1AT | 45 | 57 | + | 0 | 1 | TTTGAGGCCACAT | 14 |
| FAM069 SURECOREATSULTR11 | 99 | 105 | + | 0 | 1 | GAGACTG | |
| FAM151 INTRONLOWER | 104 | 109 | + | 0 | 1 | TGCAGG | |
| FAM002 SORLIP1AT | 113 | 125 | + | 0 | 1 | GAGGACGCCACAA | 15 |
| FAM263 DPBFCOREDCDC3 | 134 | 140 | - | 0 | 1 | ACACGGG | |
| FAM010 WBOXHVISO1 | 162 | 176 | - | 0 | 1 | TGTGACTCCCCTGGC | 16 |
| FAM270 RAV1AAT | 175 | 179 | + | 0 | 1 | CAACA | |
| FAM013 LTRECOREATCOR15 | 195 | 201 | + | 0 | 1 | TCCGACG | |
| FAM107 CGACGOSAMY3 | 197 | 201 | + | 0 | 1 | CGACG | |
| FAM147 HEXAMERATH4 | 197 | 202 | - | 0 | 1 | CCGTCG | |
| FAM149 HSELIKENTACIDICPR1 | 204 | 218 | + | 0 | 1 | CATGAAGGTTTCTAG | 17 |
| FAM149 HSELIKENTACIDICPR1 | 204 | 218 | - | 0 | 1 | CTAGAAACCTTCATG | 18 |
| FAM061 AGCBOXNPGLB | 219 | 225 | + | 0 | 1 | AGCCGCC | |
| FAM061 GCCCORE | 222 | 228 | + | 0 | 1 | CGCCGCC | |
| FAM061 GCCCORE | 225 | 231 | + | 0 | 1 | CGCCGCC | |
| FAM061 GCCCORE | 228 | 234 | + | 0 | 1 | CGCCGCC | |
| FAM061 GCCCORE | 231 | 237 | + | 0 | 1 | CGCCGCC | |
| FAM061 GCCCORE | 234 | 240 | + | 0 | 1 | CGCCGCC | |
| FAM010 WBBOXPCWRKY1 | 256 | 270 | - | 0 | 1 | TTTGACTGCTTGAAA | 19 |
| FAM325 MYBCOREATCYCB1 | 284 | 288 | + | 0 | 1 | AACGG | |
| FAM324 CGCGBOXAT | 295 | 300 | + | 0 | 1 | CCGCGC | |
| FAM324 CGCGBOXAT | 295 | 300 | - | 0 | 1 | GCGCGG | |
| FAM324 CGCGBOXAT | 297 | 302 | + | 0 | 1 | GCGCGC | |
| FAM324 CGCGBOXAT | 297 | 302 | - | 0 | 1 | GCGCGC | |
| FAM107 CGACGOSAMY3 | 322 | 326 | + | 0 | 1 | CGACG | |
| FAM147 HEXAMERATH4 | 322 | 327 | - | 0 | 1 | CCGTCG | |
| FAM243 TATABOX4 | 358 | 364 | + | 0 | 1 | TATATAA | |
| FAM241 TATABOX2 | 371 | 377 | + | 0 | 1 | TATAAAT | |
| FAM012 IBOXCORE | 381 | 387 | - | 0 | 1 | GATAAAC | |
| FAM322 BIHD1OS | 402 | 406 | - | 0 | 1 | TGTCA | |
| FAM266 MYB1AT | 411 | 416 | + | 0 | 1 | AAACCA | |
| FAM324 CGCGBOXAT | 416 | 421 | + | 0 | 1 | ACGCGC | |

TABLE 5-continued

PLACE analysis results of the 845 bp promoter p-MAWS21

| IUPAC Family | IUPAC | Start pos. | End pos. | Strand | Mismatches | Score | Sequence | SEQ ID NO: |
|---|---|---|---|---|---|---|---|---|
| FAM324 | CGCGBOXAT | 416 | 421 | − | 0 | 1 | GCGCGT | |
| FAM002 | ASF1MOTIFCAMV | 417 | 429 | + | 0 | 1 | CGCGCTGACGCGG | 20 |
| FAM324 | CGCGBOXAT | 424 | 429 | + | 0 | 1 | ACGCGG | |
| FAM324 | CGCGBOXAT | 424 | 429 | − | 0 | 1 | CCGCGT | |
| FAM012 | IBOXCORE | 432 | 438 | − | 0 | 1 | GATAATC | |
| FAM311 | EECCRCAH1 | 450 | 456 | + | 0 | 1 | GAGTTTC | |
| FAM305 | ANAERO1CONSENSUS | 460 | 466 | − | 0 | 1 | AAACAAA | |
| FAM305 | ANAERO1CONSENSUS | 466 | 472 | − | 0 | 1 | AAACAAA | |
| FAM305 | ANAERO1CONSENSUS | 473 | 479 | − | 0 | 1 | AAACAAA | |
| FAM010 | WBOXHVISO1 | 477 | 491 | − | 0 | 1 | CATGACTGGGAGAAA | 21 |
| FAM267 | TAAAGSTKST1 | 497 | 503 | + | 0 | 1 | AATAAAG | |
| FAM012 | IBOXCORENT | 510 | 516 | − | 0 | 1 | GATAAGA | |
| FAM014 | SREATMSD | 511 | 517 | + | 0 | 1 | CTTATCC | |
| FAM014 | MYBST1 | 512 | 518 | − | 0 | 1 | TGGATAA | |
| FAM273 | TATCCAOSAMY | 513 | 519 | + | 0 | 1 | TATCCAG | |
| FAM305 | ANAERO1CONSENSUS | 528 | 534 | − | 0 | 1 | AAACAAA | |
| FAM204 | PYRIMIDINEBOXHVEPB | 532 | 539 | + | 0 | 1 | TTTTTTCC | |
| FAM290 | GT1GMSCAM4 | 533 | 538 | − | 0 | 1 | GAAAAA | |
| FAM272 | SV40COREENHAN | 553 | 560 | + | 0 | 1 | GTGGAAAG | |
| FAM012 | IBOXCORENT | 567 | 573 | − | 0 | 1 | GATAAGA | |
| FAM014 | SREATMSD | 568 | 574 | + | 0 | 1 | CTTATCC | |
| FAM014 | MYBST1 | 569 | 575 | − | 0 | 1 | TGGATAA | |
| FAM273 | TATCCAOSAMY | 570 | 576 | + | 0 | 1 | TATCCAG | |
| FAM306 | ANAERO2CONSENSUS | 575 | 580 | + | 0 | 1 | AGCAGC | |
| FAM324 | CGCGBOXAT | 583 | 588 | + | 0 | 1 | GCGCGC | |
| FAM324 | CGCGBOXAT | 583 | 588 | − | 0 | 1 | GCGCGC | |
| FAM276 | TRANSINITDICOTS | 587 | 594 | − | 0 | 1 | ACCATGGC | |
| FAM272 | SV40COREENHAN | 593 | 600 | + | 0 | 1 | GTGGAAAG | |
| FAM012 | IBOXCORE | 607 | 613 | − | 0 | 1 | GATAATG | |
| FAM014 | SREATMSD | 608 | 614 | + | 0 | 1 | ATTATCC | |
| FAM014 | MYBST1 | 609 | 615 | − | 0 | 1 | AGGATAA | |
| FAM171 | MYBPZM | 612 | 618 | + | 0 | 1 | TCCTACC | |
| FAM262 | CIACADIANLELHC | 627 | 636 | − | 0 | 1 | CAAGTTCATC | 22 |
| FAM263 | DPBFCOREDCDC3 | 633 | 639 | − | 0 | 1 | ACACAAG | |
| FAM012 | IBOXCORE | 675 | 681 | − | 0 | 1 | GATAAAG | |
| FAM267 | TAAAGSTKST1 | 675 | 681 | − | 0 | 1 | GATAAAG | |
| FAM014 | SREATMSD | 676 | 682 | + | 0 | 1 | TTTATCC | |
| FAM014 | MYBST1 | 677 | 683 | − | 0 | 1 | AGGATAA | |

TABLE 5-continued

PLACE analysis results of the 845 bp promoter p-MAWS21

| IUPAC Family | IUPAC | Start pos. | End pos. | Strand | Mismatches | Score | Sequence | SEQ ID NO: |
|---|---|---|---|---|---|---|---|---|
| FAM267 | TAAAGSTKST1 | 708 | 714 | + | 0 | 1 | ATTAAAG | |
| FAM310 | CPBCSPOR | 744 | 749 | - | 0 | 1 | TATTAG | |
| FAM026 | RYREPEATLEGUMINBOX | 761 | 771 | + | 0 | 1 | AGCATGCACGC | 23 |
| FAM240 | TATABOX1 | 787 | 796 | + | 0 | 1 | CTATAAATAC | 24 |
| FAM241 | TATABOX2 | 788 | 794 | + | 0 | 1 | TATAAAT | |
| FAM100 | CCAATBOX1 | 798 | 802 | + | 0 | 1 | CCAAT | |
| FAM306 | ANAERO2CONSENSUS | 821 | 826 | + | 0 | 1 | AGCAGC | |
| FAM100 | CCAATBOX1 | 830 | 834 | + | 0 | 1 | CCAAT | |

Example 8

Binary Vector Construction for Maize Transformation to Evaluate the Function of p-MAWS21

The 845 bp promoter fragment of p-MAWS21 was amplified by PCR, incorporating a SwaI restriction enzyme site at its 5' end and a BsiWI site at its 3' end. The resulting fragment was digested and ligated into a SwaI and BsiWI digested BPS basic binary vector CB1006. Plasmid CB1006 is a plant transformation vector that comprises a plant selectable marker expression cassette (p-Ubi::c-ZmAHASL2::t-X112) as well as a promoter evaluation cassette that consists of a multiple cloning site for insertion of putative promoters via SwaI and BsiWI sites, rice MET1-1 intron to supply intron-mediated enhancement in monocot cells, GUS reporter gene, and NOS terminator. The resulting binary vector comprising the p-MAWS21::i-MET1::GUS::t-NOS expression cassette was named as RTP1054, and was used to evaluate the expression pattern driven by the p-MAWS21 promoter. FIG. 7 is a diagram of RTP1054. Sequence of the promoter cassette, p-MAWS21::i-MET1::GUS::t-NOS in binary vector RTP1054 is shown in SEQ ID NO: 25.

Example 9

Promoter Evaluation in Transgenic Maize with RTP1054

The expression patterns and levels driven by promoters p-MAWS21 were measured using GUS histochemical analysis following the protocol in the art (Jefferson 1987). Maize transformation was conducted using an *Agrobacterium*-mediated transformation system. Ten and five single copy events for T0 and T1 plants were chosen for the promoter analysis. GUS expression was measured at various developmental stages:
1) Roots and leaves at 5-leaf stage
2) Stem at V-7 stage
2) Leaves, husk and silk at flowering stage (first emergence of silk)
3) Spikelets/Tassel (at pollination)
5) Ear or Kernels at 5, 10, 15, 20, and 25 days after pollination (DAP)

Figure 3:
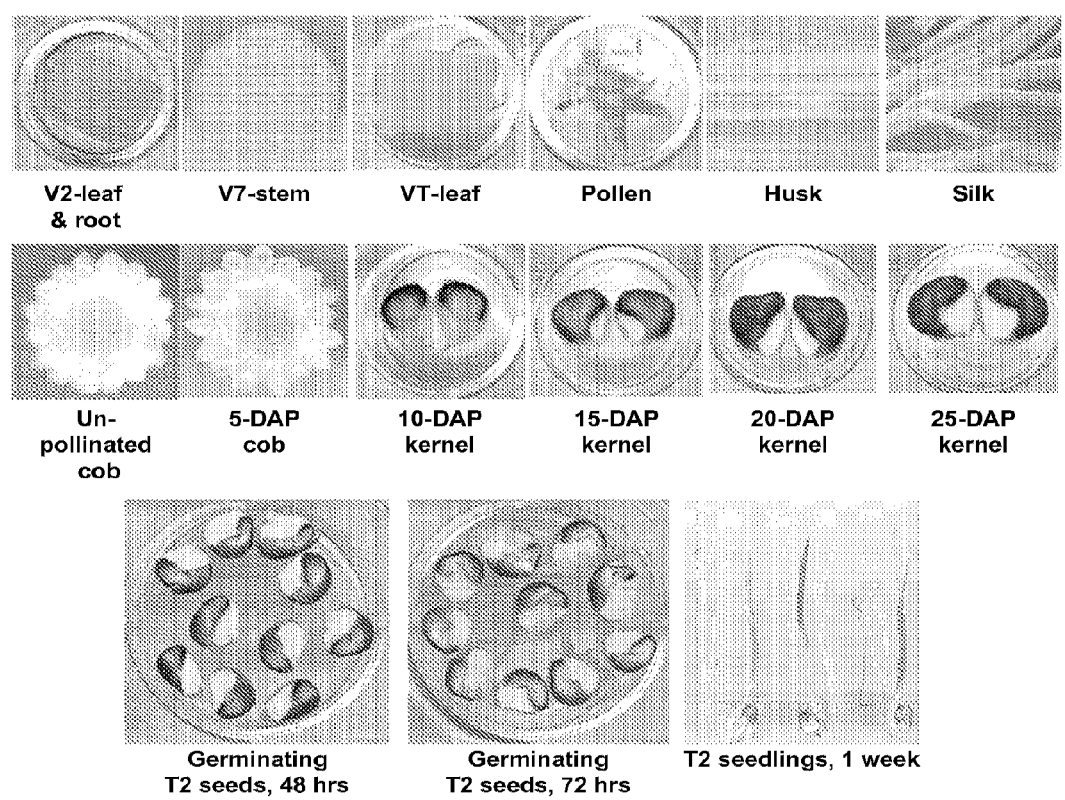
FIG. 3: GUS expression in different tissues at different developmental stages driven by p-MAWS21 in transgenic maize with RTP1054. [Root_dv: a mixture of roots at 5, 15, days after pollination (DAP); Leaf_dv: a mixture of leaves at 5, 15, 30 DAP; Ear: a mixture of ear at 5 and 10 DAP; whole seeds: a mixture of whole seeds at 15, 20, 30 DAP; Endosperm: a mixture of endosperm at 15, 20, 30 DAP; Embryo: a mixture of embryo at 15, 20, 30 DAP; Root_V2+V4: a mixture of root at V2 and V4 stages; Shoot/leaf_V2+V4: a mixture of V2 shoot and V4 leaves; Flower_GS: a mixture of flower and geminating seeds.]

The results indicated that promoter p-MAWS21 expressed specifically in pollen and in endosperm (FIG. 3).

Example 10

Generation of Transgenic *Zea mays* Plants

For generating transgenic *Zea* plants *Agrobacterium tumefaciens* (strain C58C1 [pMP90]) is transformed with the various promoter::GUS vector constructs (see below). Resulting *Agrobacterium* strains are subsequently employed to obtain transgenic plants. For this purpose a isolated transformed *Agrobacterium* colony is incubated in 4 ml culture (Medium: YEB medium with 50 µg/ml Kanamycin and 25 µg/ml Rifampicin) over night at 28° C. With this culture a 400 ml culture of the same medium is inoculated and incubated over night (28° C., 220 rpm). The bacteria a precipitated by centrifugation (GSA-Rotor, 8.000 U/min, 20 min) and the pellet is resuspended in infiltration medium (½ MS-Medium; 0.5 g/l MES, pH 5.8; 50 g/l sucrose). The suspension is placed in a plant box (Duchefa) and 100 ml SILVET L-77 (Osi Specialties Inc., Cat. P030196) are added to a final concentration of 0.02%. The plant box with 8 to 12 Plants is placed into an exsiccator for 10 to 15 min. under vacuum with subsequent, spontaneous ventilation (expansion). This process is repeated 2-3 times. Thereafter all plants are transferred into pods with wet-soil and grown under long daytime conditions (16 h light; day temperature 22-24° C., night temperature 19° C.; 65% rel. humidity). Seeds are harvested after 6 weeks.

Example 11

Growth Conditions for Plants for Tissue-Specific Expression Analysis

To obtain 4 and 7 days old seedlings, about 400 seeds (*Zea mays* ecotype Columbia) are sterilized with a 80% (v/v) ethanol:water solution for 2 minutes, treated with a sodium hypochlorite solution (0.5% v/v) for 5 minutes, washed three times with distillated water and incubated at 4° C. for 4 days to ensure a standardized germination. Subsequently, seeds are incubated on Petri dishes with MS medium (Sigma M5519) supplemented with 1% sucrose, 0.5 g/l MES (Sigma M8652), 0.8% Difco-BactoAgar (Difco 0140-01), adjusted to pH 5.7. The seedlings are grown under 16 h light/8 h dark cycle (Philips 58W/33 white light) at 22° C. and harvested after 4 or 7 days, respectively.

To obtain root tissue, 100 seeds are sterilized as described above, incubated at 4° C. for 4 days, and transferred into 250 ml flasks with MS medium (Sigma M5519) supplemented with additional 3% sucrose and 0.5 g/l MES (Sigma M8652), adjusted to pH 5.7 for further growing. The seedlings are grown at a 16 h light/8 h dark cycle (Philips 58W/33 white light) at 22° C. and 120 rpm and harvested after 3 weeks. For all other plant organs employed, seeds are sown on standard soil (Type VM, Manna-Italia, Via S. Giacomo 42, 39050 San Giacomo/Laives, Bolzano, Italien), incubated for 4 days at 4° C. to ensure uniform germination, and subsequently grown under a 16 h light/8 darkness regime (OSRAM Lumi-lux Daylight 36W/12) at 22° C. Young rosette leaves are harvested at the 8-leaf stage (after about 3 weeks), mature rosette leaves are harvested after 8 weeks briefly before stem formation. Apices of out-shooting stems are harvested briefly after out-shooting. Stem, stem leaves, and flower buds are harvested in development stage 12 (Bowmann J (ed.), *Arabidopsis*, Atlas of Morphology, Springer New York, 1995) prior to stamen development. Open flowers are harvested in development stage 14 immediately after stamen development. Wilting flowers are harvested in stage 15 to 16. Green and yellow shoots used for the analysis have a length of 10 to 13 mm.

The regenerated transgenic linseed and rape seed plants are tested in tissue culture for early leakiness. For the detailed analyses 3 individual plants per single or multi insertion line (5-15 lines in total per construct) are analyzed in the T1 to T3 generation regarding the potential expression of the promoter candidates in all non-seed tissues as well as in different phases of seed development:

Mature seeds 3 d old seedlings: root base, root tip, main root, side root, other root areas, cotyledon, hypocotyl 10 d old seedlings: root base, root tip, main root, side root, other root areas, cotyledon, hypocotyl, primary leaves, following leaves 17 d old seedlings: root base, root tip, main root, side root, other root areas, cotyledon, hypocotyl, primary leaves, following leaves Adult plant: root, young leaves, mature leaves, stem Flower 0, 1 daf, 3 daf capsula/siliques/fruit, 3 daf seed/embryo, 6 daf capsula/siliques/fruit, 6 daf seed/embryo, 9 daf capsula/siliques/fruit, 9 daf seed/embryo, 12 daf capsula/siliques/fruit, 12 daf seed/embryo, 15 daf capsula/siliques/fruit, 15 daf seed/embryo, 18 daf capsula/siliques/fruit, 18 daf seed/embryo, 21 daf capsula/siliques/fruit, 21 daf seed/embryo, 24 daf capsula/siliques/fruit, 24 daf seed/embryo alternatively, embryos from e.g. linseed capsule and rapeseed siliques are isolated from different stages of fruit development based on visual parameters and sorted to the following stages of embryo development: early, young, medium, late and mature.

The promoters are also checked for their inducibility by biotic and abiotic stress via ABA spraying on leaves.

Example 12

Demonstration of Expression Profile

To demonstrate and analyze the transcription regulating properties of a promoter of the useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-R-D-glucuronic acid during corresponding activity assays (Jefferson 1987). For determination of promoter activity and tissue specificity plant tissue is dissected, embedded, stained and analyzed as described (e.g., Bäumlein 1991).

For quantitative β-glucuronidase activity analysis MUG (methylumbelliferyl glucuronide) is used as a substrate, which is converted into MU (methylumbelliferone) and glucuronic acid. Under alkaline conditions this conversion can be quantitatively monitored fluorometrically (excitation at 365 nm, measurement at 455 nm; SpectroFluorimeter Thermo Life Sciences Fluoroscan) as described (Bustos 1989).

The invention claimed is:

1. An expression cassette for regulating seed-specific expression of a polynucleotide of interest, said expression cassette comprising a transcription regulating nucleotide sequence selected from the group consisting of:
   (a) the nucleic acid sequence of SEQ ID NO: 1; and
   (b) a nucleic acid sequence which has at least 95% sequence identity to the nucleic acid sequence of SEQ ID NO: 1;
   wherein said polynucleotide of interest is heterologous to said transcription regulating nucleotide sequence.

2. A vector comprising the expression cassette of claim 1.

3. The vector of claim 2, wherein said vector is an expression vector.

4. A non-human host cell comprising the expression cassette of claim 1 or a vector comprising said expression cassette.

5. The non-human host cell of claim 4, wherein said non-human host cell is a plant cell.

6. A transgenic plant tissue, plant organ, plant, or seed comprising the expression cassette of claim 1 or a vector comprising said expression cassette.

7. The transgenic plain tissue, plant organ, plant, or seed of claim 6, wherein said transgenic plant tissue, plant organ, plant, or seed is a monocotyledonous plant tissue, plant organ, plant, or seed.

8. A method for expressing a polynucleotide of interest in a non-human host cell comprising:
   (a) introducing the expression cassette of claim 1 or a vector comprising said expression cassette into a non-human host cell, and
   (b) expressing the at least one polynucleotide of interest in said non-human host cell.

9. The method of claim 8, wherein the non-human host cell is a plant cell.

10. A method for producing a transgenic plant tissue, plant organ, plant, or seed comprising:
    (a) introducing the expression cassette of claim 1 or a vector comprising said expression cassette into a plant cell; and
    (b) regenerating said plant cell to form a plant tissue, plant organ, plant, or seed.

11. The method of claim 10, wherein the method further comprises selecting the plant cell for the presence of the expression cassette of claim 1 or the vector comprising said expression cassette.

12. The expression cassette of claim 1, wherein said transcription regulating nucleotide sequence has at least 98% sequence identity to the nucleic acid sequence of SEQ ID NO: 1.

* * * * *